US012653856B2

(12) United States Patent
Moon et al.

(10) Patent No.: US 12,653,856 B2

(45) Date of Patent: Jun. 16, 2026

(54) ***GYNOSTEMMA PENTAPHYLLUM* TEA OR *GYNOSTEMMA PENTAPHYLLUM* TEA EXTRACT CONTAINING GYPENOSIDE L AND GYPENOSIDE LI AND ANTIOBESITY USE THEREOF**

(71) Applicant: BIONIC TRADING CORPORATION, Gyeonggi-do (KR)

(72) Inventors: Joo Myung Moon, Gyeonggi-do (KR); Hyung Joong Kim, Gyeonggi-do (KR); Jung Eun Gwag, Gyeonggi-do (KR); Seung Beom Yun, Incheon (KR); Tae Young Kim, Gyeonggi-do (KR)

(73) Assignee: BIONIC TRADING CORPORATION, Gyeonggi-do (KR)

(*) Notice: Subject to any disclaimer, the term of this patent is extended or adjusted under 35 U.S.C. 154(b) by 273 days.

(21) Appl. No.: 18/519,895

(22) Filed: Nov. 27, 2023

(65) Prior Publication Data

US 2024/0108675 A1 Apr. 4, 2024

Related U.S. Application Data

(63) Continuation-in-part of application No. PCT/KR2021/014739, filed on Oct. 20, 2021.

(30) Foreign Application Priority Data

May 28, 2021 (KR) ........................ 10-2021-0069046
Sep. 3, 2021 (KR) ........................ 10-2021-0117721

(51) Int. Cl.

| | |
|---|---|
| ***A61K 36/00*** | (2006.01) |
| ***A61K 31/704*** | (2006.01) |
| ***A61K 36/424*** | (2006.01) |
| ***A61P 3/04*** | (2006.01) |

(52) U.S. Cl.

CPC .......... *A61K 36/424* (2013.01); *A61K 31/704* (2013.01); *A61P 3/04* (2018.01); *A61K 2236/17* (2013.01); *A61K 2236/331* (2013.01)

(58) Field of Classification Search

CPC ........................................................ A61P 3/04

See application file for complete search history.

(56) References Cited

U.S. PATENT DOCUMENTS

2019/0201468 A1* 7/2019 Kim .................... A61K 36/424

FOREIGN PATENT DOCUMENTS

| | | |
|---|---|---|
| JP | S5933337 | 8/1984 |
| KR | 10-2008-0017963 | 2/2008 |
| KR | 10-2010-0130020 | 12/2010 |
| KR | 10-2016-0000657 | 1/2016 |
| KR | 10-2019-0010506 | 1/2019 |

OTHER PUBLICATIONS

Piao, X.L., et al., "Dammarane-type saponins from heat-processed Gynostemma pentaphyllum show fortified activity against A549 cells", Arch. Pharm. Res. (2013) 36:874-879.

Chen, D.-J., et al., "Metabolic profiling of Gynostemma pentaphyllum extract in rat serum, urine and faeces after oral administration," ournal of Chromatography B (2014), http://dx.doi.org/10.1016/j.jchromb.2014.08.003.

* cited by examiner

*Primary Examiner* — Qiuwen Mi

(74) *Attorney, Agent, or Firm* — DUANE MORRIS LLP; Gregory M. Lefkowitz; Brandon A. Chan

(57) ABSTRACT

A composition for antiobesity, which contains a *Gynostemma pentaphyllum* tea or a *Gynostemma pentaphyllum* tea extract as an active ingredient is provided. The composition contains a *Gynostemma pentaphyllum* tea or a *Gynostemma pentaphyllum* tea extract as an active ingredient, is effective for preventing, alleviating or treating diabetes, obesity, muscle loss, etc. since it exhibits the efficacy of increasing AMPK activity, promoting beta oxidation, promoting glucose uptake, etc. In addition, since the composition is derived from a natural product, it can be safely used as a drug, food, etc. without side effects.

9 Claims, 2 Drawing Sheets

*GYNOSTEMMA PENTAPHYLLUM* TEA OR *GYNOSTEMMA PENTAPHYLLUM* TEA EXTRACT CONTAINING GYPENOSIDE L AND GYPENOSIDE LI AND ANTIOBESITY USE THEREOF

CROSS-REFERENCE TO RELATED APPLICATIONS

This application is a bypass continuation-in-part of International Application No. PCT/KR2021/014739 filed on Oct. 20, 2021, which claims priority to Korean Patent Application No. 10-2021-0069046 filed on May 28, 2021, and Korean Patent Application No. 10-2021-0117721 filed on Sep. 3, 2021, the entireties of which are incorporated herein by reference.

TECHNICAL FIELD

The present disclosure relates to a *Gynostemma pentaphyllum* tea or a *Gynostemma pentaphyllum* tea extract containing gypenoside L and gypenoside LI and antiobesity use thereof.

BACKGROUND ART

The present disclosure relates to a composition having antiobesity effect by degrading and reducing body fat. The accumulation of fat in the body can lead to obesity. The obesity refers to a condition in which excess fat is accumulated in the body due to imbalance between energy intake and consumption, which can cause various health problems. Its causes include excessive calorie intake, lack of exercise, endocrine disorders, genetic factors, etc.

Recently, with the improved living standards of the modern people, the rapid increase of patients with obesity and obesity-related disease worldwide is becoming a social issue. According to the World Health Organization (WHO) statistics in 2016, 2 billion adults who are 18 years or older are overweight and, among them, as many as 650 million people have obesity. Obesity is also considered as the factor that causes cancer and metabolic syndromes such as diabetes, cardiovascular diseases, type 2 diabetes, hypertension, arteriosclerosis, etc.

There have been efforts to improve the obesity using drugs. The drugs for improving obesity are classified into appetite suppressants and fat absorption inhibitors depending on the mechanism of action. Phentermine and diethylpropion that suppress appetite have side effects such as increased blood pressure, dizziness, headache, tremor, dry mouth, etc. and sibutramine has cardiovascular side effects. The fat absorption inhibitor orlistat has side effects such as inhibited absorption of fat-soluble vitamins, steatorrhea, fat discharge, frequent bowel movement and fecal incontinence.

In addition, the above drugs have problems that they are not helpful for those who are obese already.

Recently, the need for the study of drugs or foods which are safe and have superior antiobesity efficacy has been raised for the prevention and treatment of obesity. In particular, researches on natural functional substances or methods with few side effects are being carried out actively.

The inventors of the present disclosure have researched to find a natural product which has few side effects while exhibiting antiobesity effect. As a result, they have prepared a *Gynostemma pentaphyllum* tea or a *Gynostemma pentaphyllum* tea extract with significantly increased effect of reducing body fat and have completed the present disclosure.

REFERENCES OF RELATED ART

Patent Documents (Patent document 001) KR 10-1969062 B.

DISCLOSURE

Technical Problem

The present disclosure is directed to providing a method for treating obesity by administering a composition containing a *Gynostemma pentaphyllum* tea or a *Gynostemma pentaphyllum* tea extract, which contains gypenoside L and gypenoside LI at a weight ratio of 100:20-80.

The present disclosure is also directed to providing a method for preparing a *Gynostemma pentaphyllum* tea or a *Gynostemma pentaphyllum* tea extract for antiobesity, wherein the *Gynostemma pentaphyllum* tea or the *Gynostemma pentaphyllum* tea extract contains gypenoside L and gypenoside LI at a weight ratio of 100:20-80.

Technical Solution

The present disclosure provides a method for treating obesity by administering a composition comprising a *Gynostemma pentaphyllum* tea or a *Gynostemma pentaphyllum* tea extract, which comprises gypenoside L and gypenoside LI at a weight ratio of 100:20-80.

In addition, the present disclosure provides a method for preparing a *Gynostemma pentaphyllum* tea or a *Gynostemma pentaphyllum* tea extract for antiobesity, which includes: (1) a step of putting dried *Gynostemma pentaphyllum* leaf in a reaction vessel and supplying 0.1-10 parts by weight of water based on 1 part by weight of the dried *Gynostemma pentaphyllum* leaf; (2) a step of swelling the *Gynostemma pentaphyllum* leaf while heating the reaction vessel from 100 to 150° C. at a rate of 0.2-10° C./min; (3) a step of heating the reaction vessel at 100-150° C. for 2 minutes to 24 hours; and (4) a step of drying the *Gynostemma pentaphyllum* leaf by releasing the pressure of the reaction vessel, wherein the *Gynostemma pentaphyllum* tea or the *Gynostemma pentaphyllum* tea extract contains gypenoside L and gypenoside LI at a weight ratio of 100:20-80.

Advantageous Effects

A composition of the present disclosure, which contains a *Gynostemma pentaphyllum* tea or a *Gynostemma pentaphyllum* tea extract as an active ingredient, is effective for preventing, alleviating or treating diabetes, obesity, muscle loss, etc. since it exhibits the efficacy of increasing AMPK activity, promoting beta oxidation, promoting glucose uptake, etc.

In addition, since the composition of the present disclosure is derived from a natural product, it can be safely used as a drug, food, etc. without side effects.

BEST MODE

Figure 1:
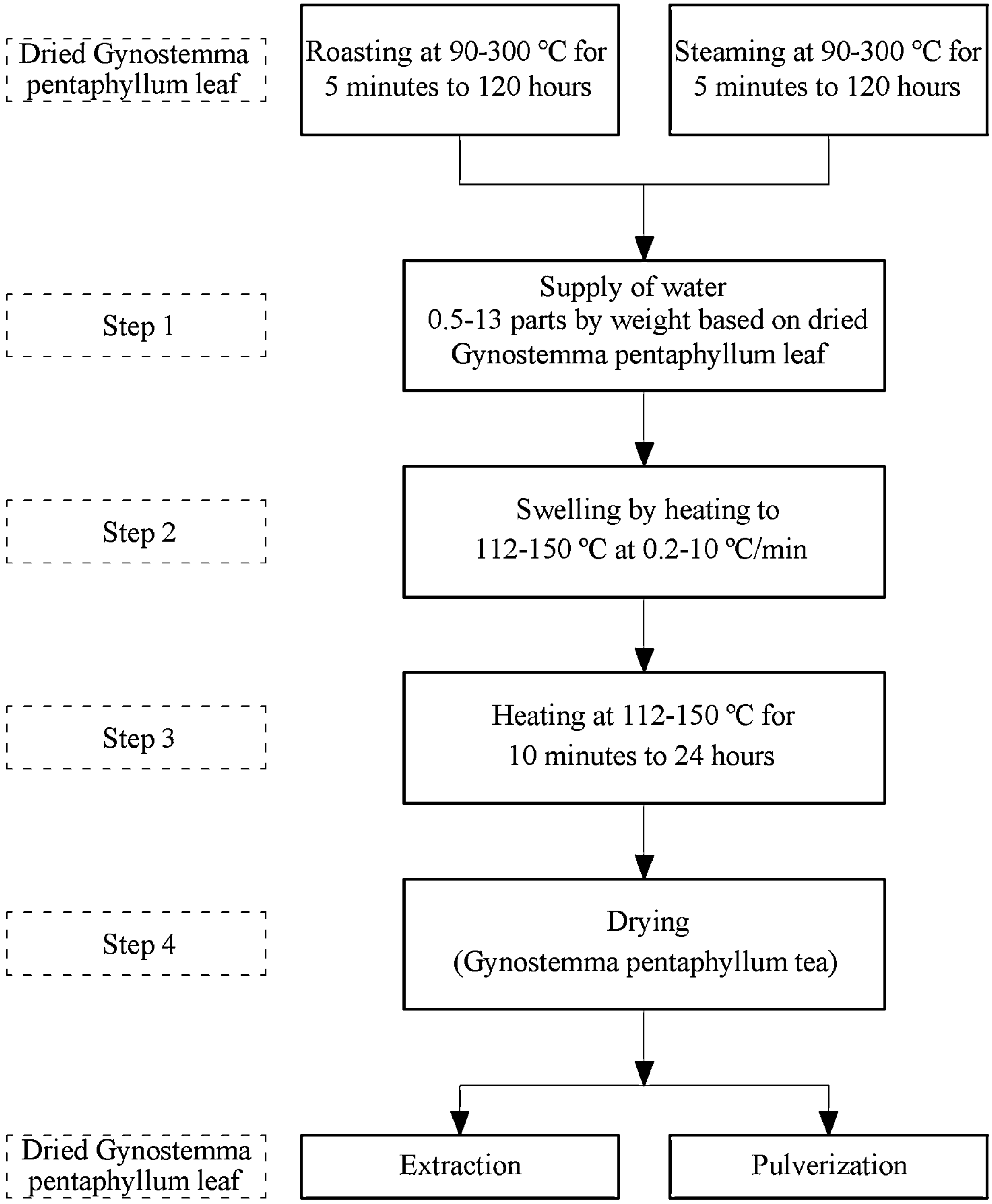
FIG. 1 is a process chart describing a method for preparing a *Gynostemma pentaphyllum* tea extract according to an exemplary embodiment of the present disclosure.

Hereinafter, the present disclosure is described in detail.

*Gynostemma pentaphyllum* is a perennial vine belonging to the family Cucurbitaceae. It grows wildly in mountains or fields. The rhizome extends sideways, has white hairs and grows entangled or climbs with tendrils. It grows wildly in the mountains of the southern part, Jeju Island and Ulleungdo of Korea and is distributed widely overseas in China, Japan, Southeast Asia, etc. It grows mainly in the humid areas such as shores and riversides.

There are several species of *Gynostemma* depending on countries and regions. About 30 species are known and it is known that they vary greatly in ingredients and contents thereof depending on the regions where they grow. Among them, the species *pentaphyllum* is distributed widely and its ingredients and effects have been studied extensively. *Gynostemma pentaphyllum* contains various saponins, which are called gynosaponins or gypenosides. The gypenosides have chemical structures similar to those of ginseng ginsenosides except for the position where the OH group is bonded. Due to the high saponin contents of *Gynostemma pentaphyllum, Gynostemma pentaphyllum* leaf has been widely used as an energy drink, as a substitute for ginseng, from old times.

It is known that *Gynostemma pentaphyllum* saponins have the efficacy of improving lipid metabolism, protecting against cardiovascular diseases, lowering blood sugar and acting on the central nervous system, as well as anticancer, platelet aggregation-inhibiting and tonifying actions. In addition to gypenosides, *Gynostemma pentaphyllum* contains glycosides such as primeveroside, sophoroside, bisdesmoside, gentiobioside, rutinoside, etc., steroids, sugars, pigments, etc.

In the present specification, "*Gynostemma pentaphyllum* tea" may be prepared by processing *Gynostemma pentaphyllum* leaf with various methods. Specifically, it may be prepared by swelling roasted *Gynostemma pentaphyllum* leaf, and heating and then drying the swollen *Gynostemma pentaphyllum* leaf. Since the *Gynostemma pentaphyllum* tea of the present disclosure prepared by the method described above contains gypenoside L and gypenoside LI at a weight ratio of 100:20-80, it has further enhanced antiobesity efficacy.

In the present specification, "*Gynostemma pentaphyllum* tea extract" is obtained by extracting the *Gynostemma pentaphyllum* tea prepared by processing *Gynostemma pentaphyllum* leaf with various methods and may also be referred to as *Gynostemma pentaphyllum* leaf tea, *Gynostemma pentaphyllum* leaf tea extract or *Gynostemma pentaphyllum* leaf extract.

In the present specification, the "gypenoside" refers to a triterpenoid saponin.

In the present specification, "obesity" refers to a condition in which the proliferation and differentiation of adipocytes are increased due to metabolic disorders and, as a result, fat is accumulated excessively. It may cause complications including metabolic syndrome accompanied by hypertension, diabetes, dyslipidemia, etc. Men are considered obese when body fat percentage is 25% or higher of body weight, and women are considered obese when it is 30% or higher of body weight. Clinically, the state where the BMI (body mass index) is 25.0-30.0 is defined as overweight and the state where it is 30.0 or higher is defined as obese.

In the present specification, "antiobesity" includes the prevention, alleviation or treatment of obesity and includes the reduction of body fat and/or reduction of body weight.

In the present specification, "prevention" means suppressing or delaying of the progression of the symptoms of obesity by administering the composition of the present disclosure.

In the present specification, "alleviation" refers to improving the parameters related with obesity, e.g., the symptoms of obesity, by administering the composition of the present disclosure.

In the present specification, "treatment" means, unless specified otherwise, reversing, alleviating, suppressing the progression, or preventing the symptoms of obesity.

The present disclosure provides a food composition for antiobesity, which contains a *Gynostemma pentaphyllum* tea or a *Gynostemma pentaphyllum* tea extract (hereinafter, collectively referred to as "*Gynostemma pentaphyllum* tea") containing gypenoside L and gypenoside LI at a weight ratio of 100:20-80 as an active ingredient.

The gypenoside L is a compound represented by Chemical Formula 1.

[Chemical Formula 1]

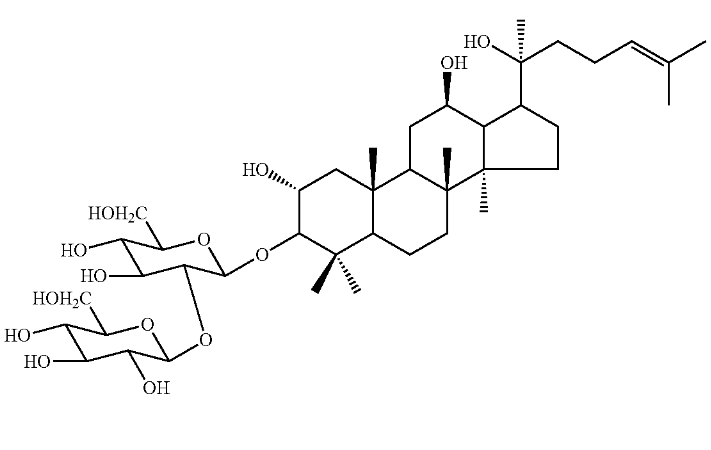

And, the gypenoside LI, which is a diastereomer of the gypenoside L, is a compound represented by Chemical Formula 2.

[Chemical Formula 2]

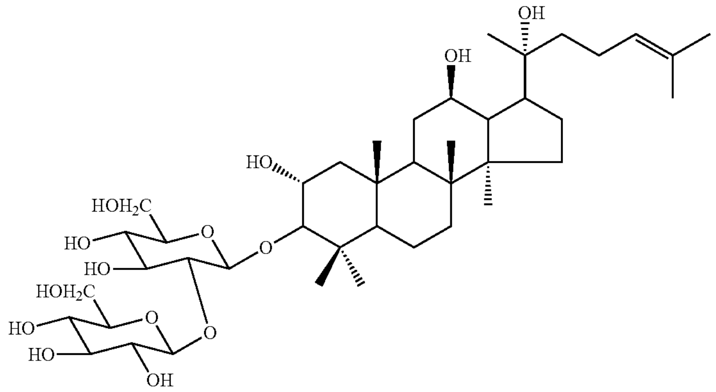

The weight ratio of the gypenoside L and the gypenoside LI may be 100:20-80, specifically 100:30-70, more specifically 100:50-70, more specifically 100: 55-65.

When the weight ratio of the gypenoside L and the gypenoside LI is within the above ranges, the antiobesity effect of the *Gynostemma pentaphyllum* tea is maximized. If the weight ratio of the gypenoside L and the gypenoside LI is below the lower limit, the antiobesity effect of the *Gynostemma pentaphyllum* tea may be insignificant. And, if it exceeds the upper limit, the antiobesity effect of the *Gynostemma pentaphyllum* tea, particularly the effect of reducing body fat, may be decreased on the contrary.

The *Gynostemma pentaphyllum* tea of the present disclosure may contain the gypenoside L and the gypenoside LI at a content of 20-140 mg/g, specifically 25-140 mg/g, more specifically 30-120 mg/g, more specifically 30-100 mg/g, specifically 30-60 mg/g. When the content of gypenoside L and gypenoside LI contained in the *Gynostemma pentaphyllum* tea is within the above ranges, the antiobesity effect of the *Gynostemma pentaphyllum* tea is maximized. If the content of gypenoside L and gypenoside LI contained in the *Gynostemma pentaphyllum* tea is below the lower limit, the antiobesity effect of the *Gynostemma pentaphyllum* tea may be insignificant. And, if it exceeds the upper limit, the antiobesity effect of the *Gynostemma pentaphyllum* tea may be decreased on the contrary.

The *Gynostemma pentaphyllum* tea may contain the gypenoside L at a content of 10-80 mg/g, specifically 15-80 mg/g, more specifically 20-60 mg/g, and may contain the gypenoside LI at a content of 10-60 mg/g, specifically 12-48 mg/g. When the contents of gypenoside L and gypenoside LI contained in the *Gynostemma pentaphyllum* tea are within the above ranges, the antiobesity effect of the *Gynostemma pentaphyllum* tea may be maximized.

The *Gynostemma pentaphyllum* tea may further contain 5-10 parts by weight of Rg3 based on 100 parts by weight of the gypenoside L and the gypenoside LI.

When the weight ratio of Rg3 in the *Gynostemma pentaphyllum* tea based on gypenoside L and gypenoside LI is within the range, the antiobesity effect of the *Gynostemma pentaphyllum* tea is increased further. If the weight ratio of Rg3 based on the gypenoside L and the gypenoside LI is below the lower limit, the antiobesity effect of the *Gynostemma pentaphyllum* tea may be decreased.

In addition, the *Gynostemma pentaphyllum* tea may further contain 50-90 parts by weight, specifically 60-80 parts by weight, of damulin A and damulin B based on 100 parts by weight of the gypenoside L and the gypenoside LI.

When the weight ratio of damulin A and damulin B based on the gypenoside L and the gypenoside LI in the *Gynostemma pentaphyllum* tea is within the above ranges, the antiobesity effect of the *Gynostemma pentaphyllum* tea is increased further.

The *Gynostemma pentaphyllum* tea of the present disclosure may contain 0.5-14 mg/g of ginsenoside Rg3, 10-80 mg/g of gypenoside L, 10-60 mg/g of gypenoside LI, 10-20 mg/g of damulin A, 10-20 mg/g of damulin B and 10 ppb or less of benzopyrenes.

The *Gynostemma pentaphyllum* tea of the present disclosure may be prepared by a method including: a step of swelling dried *Gynostemma pentaphyllum* leaf; and a step of heating and then drying the swollen *Gynostemma pentaphyllum* leaf.

The inventors of the present disclosure have swollen dried *Gynostemma pentaphyllum* leaf sufficiently by supplying water and converted high-glycoside saponin to low-glycoside saponin sufficiently by treating at high temperature in wet state for a predetermined time. It was confirmed that, when the swollen *Gynostemma pentaphyllum* leaf is heat-treated by the method of the present disclosure, the conversion of proteins, carbohydrates and lipids contained in the *Gynostemma pentaphyllum* leaf to benzopyrenes is decreased and the contents of low-molecular-weight effective saponins such as Rg3, gypenoside L, gypenoside LI, damulin A, damulin B, etc. are increased. In particular, according to the present disclosure, a *Gynostemma pentaphyllum* tea containing gypenoside L and gypenoside LI at a weight ratio of 100:20-80, which contains gypenoside L and gypenoside LI at a content of 20-140 mg/g, specifically 25-140 mg/g, can be prepared. The benzopyrene is formed during heat treatment at high temperature following the roasting, steaming or swelling of *Gynostemma pentaphyllum* leaf. A *Gynostemma pentaphyllum* tea with a decreased benzopyrene content can be prepared since benzopyrene are evaporated together with water vapor when the pressure of a (sealed) reaction vessel is released.

In the present specification, the low-molecular-weight effective saponin is also referred to as "low-glycoside saponin" or "low-molecular-weight saponin".

More specifically, the *Gynostemma pentaphyllum* tea of the present disclosure may be prepared by a method including the steps (1)-(4) described below.

The inventors of the present disclosure have consistently researched on a method for preparing a *Gynostemma pentaphyllum* tea having antiobesity effect. As a result, they have identified that a *Gynostemma pentaphyllum* tea prepared by a method including: (1) a step of putting dried *Gynostemma pentaphyllum* leaf in a reaction vessel and supplying 0.1-10 parts by weight of water based on 1 part by weight of the dried *Gynostemma pentaphyllum* leaf; (2) a step of swelling the *Gynostemma pentaphyllum* leaf while heating the reaction vessel from 100 to 150° C. at a rate of 0.2-10° C./min; (3) a step of heating the reaction vessel at 100-150° C. for 2 minutes to 24 hours; and (4) a step of drying the *Gynostemma pentaphyllum* leaf by releasing the pressure of the reaction vessel has remarkably increased antiobesity effect, and have completed the present disclosure.

First, in the step (1), dried *Gynostemma pentaphyllum* leaf is put in a reaction vessel and 0.1-10 parts by weight of water is supplied based on 1 part by weight of the dried *Gynostemma pentaphyllum* leaf. The reaction vessel may be a pressurized sealed container. In the present disclosure, the reaction vessel is sealed after the dried *Gynostemma pentaphyllum* leaf and water are supplied.

The dried *Gynostemma pentaphyllum* leaf refers to *Gynostemma pentaphyllum* leaf that has been dried, and includes naturally dried *Gynostemma pentaphyllum* leaf, semi-dried *Gynostemma pentaphyllum* leaf, *Gynostemma pentaphyllum* leaf that has been dried after roasting or steaming, etc.

Specifically, the dried *Gynostemma pentaphyllum* leaf may be obtained by roasting or steaming fresh *Gynostemma pentaphyllum* leaf at 90-300° C. for 5 minutes to 120 hours and then drying the same.

Since most of the precursors of the active substances of the *Gynostemma pentaphyllum* leaf are glycosides, it is expected in principle that application of high-temperature heat will break the bonds of sugar or lipid ingredients in the *Gynostemma pentaphyllum* leaf, thereby increasing the contents of active ingredients. In addition, the application of high-temperature heat such as roasting can suppress compositional change over time as much as possible by inactivating degradative enzymes contained in the *Gynostemma pentaphyllum* leaf.

In general, roasting is a process of heat-treating fresh leaf in an open container above a predetermined temperature to prevent spoilage by sterilizing harmful bacteria and to improve storability, aroma and flavor by inactivating the activity of degradative enzymes remaining in the fresh leaf. The roasting results in excessive production of benzopyrenes due to uneven temperatures or uneven conversion of precursors to active ingredients as well as decreased conversion to low-molecular-weight effective saponins due to water loss.

Accordingly, in the present disclosure, the roasting or steaming may be performed at 90-300° C., specifically 90-200° C., more specifically 90-150° C., for 20 minutes to 120 hours, specifically 30 minutes to 30 hours, more specifically 1-10 hours. When the roasting or steaming is performed within the above temperature ranges, the production of benzopyrenes can be reduced while preventing the loss of active ingredients contained in the *Gynostemma pentaphyllum* leaf.

In addition, the heating such as roasting or steaming may be more preferably performed by roasting in terms of reduction of benzopyrene contents and increase of active substance contents. The roasting may be performed by roasting with wood fire, roasting with gas fire, roasting with an electric heater, etc. although not being specially limited thereto. The roasting with wood fire may be performed by roasting the *Gynostemma pentaphyllum* leaf in a pot heated with wood fire. The roasting with gas fire may be performed by roasting the *Gynostemma pentaphyllum* leaf in a pot heated with medium gas fire. The roasting with an electric heater may be performed by roasting the *Gynostemma pentaphyllum* leaf in a cylinder of a rotating electric heater. Among these methods, the roasting with an electric heater is more preferable in terms of increasing the contents of active substances while reducing the contents of benzopyrenes.

If the *Gynostemma pentaphyllum* leaf is merely dried naturally without roasting, the high-glycoside saponins may hardly be converted to low-molecular-weight effective saponins.

The inventors of the present disclosure have found out that the fresh *Gynostemma pentaphyllum* leaf should be heat-treated by roasting, etc. in order to increase the contents of low-molecular-weight effective saponins of the leaf as much as possible. In addition, based on the relationship between saponin precursors and low-molecular-weight effective saponins (Chen et al., *J. Chromatogr. B Analyt Technol Biomed life Sci,* 969: pp. 42-52), it was estimated that, when the fresh leaf of *Gynostemma pentaphyllum* is roasted, the total amount of saponins can be maintained as the enzymes that degrade saponins are inactivated and the saponins are converted to low-molecular-weight effective saponins by high-temperature heat treatment.

The dried *Gynostemma pentaphyllum* leaf may have a water content of 0.01-70 wt %, specifically 0.02-50 wt %, more specifically 0.03-15 wt %.

In the present disclosure, 0.1-10 parts by weight, specifically 0.1-5 parts by weight, more specifically 0.1-3 parts by weight, more specifically 0.1-2 parts by weight, more specifically 0.1-1 parts by weight, more specifically 0.2-0.8 parts by weight, of water may be supplied based on 1 part by weight of the dried *Gynostemma pentaphyllum* leaf. For the fresh *Gynostemma pentaphyllum* leaf which has been dried not enough after the roasting, the amount of the added water may be reduced.

The reason why water is supplied to the dried *Gynostemma pentaphyllum* leaf is to sufficiently swell the *Gynostemma pentaphyllum* leaf by increasing the water content of the *Gynostemma pentaphyllum* leaf. That is to say, in the present disclosure, water is supplied to the *Gynostemma pentaphyllum* leaf only to "swell" the *Gynostemma pentaphyllum* leaf and this is entirely different from "immersion" wherein the *Gynostemma pentaphyllum* leaf is completely submerged in a solvent or "extraction" whereby the active ingredients of the *Gynostemma pentaphyllum* leaf are eluted by sufficiently supplying a solvent. When the *Gynostemma pentaphyllum* leaf is swollen enough, the conversion rate of high-glycoside saponins to low-molecular-weight effective saponins is increased significantly in the subsequent heat treatment step.

Accordingly, in the present disclosure, the amount of water supplied to the *Gynostemma pentaphyllum* leaf is of great importance. The amount of the supplied water should be sufficient to allow the *Gynostemma pentaphyllum* leaf to absorb water and "swell" enough. If water is supplied in excess, the active ingredients contained in the *Gynostemma pentaphyllum* leaf may be eluted undesirably.

If the amount of water is below the lower limit, the *Gynostemma pentaphyllum* leaf may not be swollen enough and the conversion to low-molecular-weight effective saponins in the subsequent heat treatment step may be insufficient. And, if it exceeds the upper limit, the contents of low-molecular-weight effective saponins contained in the *Gynostemma pentaphyllum* leaf may decrease as the effective saponins contained in the *Gynostemma pentaphyllum* leaf are eluted. Furthermore, it is uneconomical because a lot of time and utility cost are spent in the subsequent drying process.

Next, in the step (2), the reaction vessel is heated to 100-150° C., specifically 112-150° C., more specifically 115-130° C., more specifically 120-130° C., at a rate of 0.2-10° C./min, specifically 0.2-5° C./min, more specifically 0.2-2.5° C./min, more specifically 0.5-2.5° C./min, more specifically 0.5-1.5° C./min. This step is for swelling the dried *Gynostemma pentaphyllum* leaf sufficiently.

If the heating rate is below the lower limit, it takes too long time to reach the target temperature. And, if it exceeds the upper limit, the *Gynostemma pentaphyllum* leaf may not be swollen enough. In addition, if the heating is not performed under the above conditions, the dried *Gynostemma pentaphyllum* leaf may not be swollen enough.

Through the heating, the *Gynostemma pentaphyllum* leaf is swollen enough and the water content in the *Gynostemma pentaphyllum* leaf reaches 10-100%, specifically 60-95%, more specifically 70-90%, more specifically 75%-85%. As a result, the conversion of high-glycoside saponins to low-molecular-weight effective saponins in the subsequent heating step can be achieved more easily.

If the water content in the *Gynostemma pentaphyllum* leaf is below the lower limit, the conversion of high-glycoside saponins to low-molecular-weight effective saponins in the subsequent heating step may not be achieved easily because of insufficient swelling of the *Gynostemma pentaphyllum* leaf. And, the water content exceeding the upper limit is undesirable in terms of economy because of low cost-effectiveness to increase the water content in the *Gynostemma pentaphyllum* leaf.

Next, in the step (3), the reaction vessel is heated at 100-150° C. for 2 minutes to 24 hours. Through the heating, the low-molecular-weight effective saponin precursors in the *Gynostemma pentaphyllum* leaf which has been swollen by absorbing water in the step (2) may be converted to low-molecular-weight effective saponin through hydrolysis. In addition, the benzopyrenes contained in the *Gynostemma pentaphyllum* leaf are evaporated.

The heating temperature may be 100-150° C., specifically 112-150° C., more specifically 115-135° C., more specifically 120-135° C., more specifically 120-130° C. If the heating temperature is below the lower limit, the conversion rate of low-molecular-weight effective saponin precursors to low-molecular-weight effective saponins is decreased and the conversion time is increased. And, if it exceeds the upper limit, there may occur problems in terms of energy efficiency and safety as well as degradation of saponins and increase of benzopyrenes.

In addition, the heating time may be 2 minutes to 24 hours, specifically 2 minutes to 12 hours, more specifically 2 minutes to 10 hours, more specifically 2 minutes to 8 hours, more specifically 2 minutes to 6 hours, more specifically 2 minutes to 4 hours.

If the heating time is below the lower limit, the conversion rate of low-molecular-weight effective saponin precursors to low-molecular-weight effective saponins may be decreased and the evaporation of benzopyrenes may be decreased. And, if it exceeds the upper limit, the contents of low-molecular-weight effective saponins are decreased due to degradation and the contents of benzopyrenes are increased.

As specific examples of the heating treatment, when the heating temperature is 120° C., the heating time may be 1-12 hours, specifically 4-8 hours, specifically 2-4 hours, when the heating temperature is 130° C., the heating time may be 30 minutes to 4 hours, specifically 1-3 hours, when the heating temperature is 140° C., the heating time may be 20 minutes to 3 hours, specifically 30 minutes to 2 hours, and when the heating temperature is 150° C., the heating time may be 2 minutes to 24 hours, specifically 2 minutes to 12 hours, more specifically 2 minutes to 8 hours, more specifically 2 minutes to 6 hours, more specifically 2 minutes to 4 hours.

Next, in the step (4), the *Gynostemma pentaphyllum* leaf is dried by releasing the pressure of the reaction vessel. Because the reaction vessel is in a state where the temperature and pressure in the reaction vessel have been raised through the heating in the step (3), if the pressure of the reaction vessel is released, the *Gynostemma pentaphyllum* leaf is dried under reduced pressure as the water vapor in the reaction vessel is evaporated quickly. At the same time, benzopyrenes are also evaporated and discharged together.

As a result, the *Gynostemma pentaphyllum* leaf is in semi-dried state where the water content is below 80 wt %, specifically 30-75 wt %, more specifically 30-50 wt %.

The *Gynostemma pentaphyllum* tea of the present disclosure may be prepared by adding (4-1) a step of further drying the dried *Gynostemma pentaphyllum* leaf after the step (4).

The drying may be performed by hot air drying, freeze-drying, vacuum drying, drying under reduced pressure, natural drying, etc. without any limitation.

The drying may be performed until the water content of the *Gynostemma pentaphyllum* leaf becomes less than 30 wt %, specifically 0.1-15 wt %.

In another specific exemplary embodiment, the *Gynostemma pentaphyllum* tea extract of the present disclosure may be prepared by further adding (5) a step of extracting the dried *Gynostemma pentaphyllum* leaf at 40-100° C. using hot water or ethanol.

In the step (5), the *Gynostemma pentaphyllum* leaf dried in the step (4) is extracted at 40-100° C., specifically 50-100° C., more specifically 70-100° C., more specifically 80-100° C. under normal pressure using hot water or ethanol. If the extraction temperature is below the lower limit, the extraction efficiency of low-molecular-weight effective saponins may be decreased. And, the extraction temperature exceeding the upper limit is undesirable in terms of economy because of low cost-effectiveness to increase the temperature.

Specifically, the extraction in the step (5) may be repeated twice. The first extraction may be performed at 40-100° C. using hot water and the second extraction may be performed using 40-80% (v/v) ethanol to increase extraction yield and increase the contents of saponins in the *Gynostemma pentaphyllum* leaf extract. In order to increase the saponin content of the *Gynostemma pentaphyllum* leaf extract, ethanol aqueous solvent may be used as an extraction solvent for both the first and second extractions and the number of extraction may exceed twice, although it is not desirable in terms of cost-effectiveness.

Since the prepared *Gynostemma pentaphyllum* tea or *Gynostemma pentaphyllum* tea extract of the present disclosure contains gypenoside L and gypenoside LI at a weight ratio of 100:20-80, specifically 100:30-70, more specifically 100:50-70, more specifically 100:55-65, and contains 20-140 mg/g, specifically 25-140 mg/g, more specifically 30-120 mg/g, more specifically 30-100 mg/g, specifically 30-60 mg/g, of gypenoside L and gypenoside LI, it has very superior antiobesity effect. In addition, the *Gynostemma pentaphyllum* tea or *Gynostemma pentaphyllum* tea extract of the present disclosure is very useful because the contents of low-molecular-weight effective saponins such as ginsenoside Rg3, gypenoside L, gypenoside LI, damulin A, damulin B, etc. are high, extraction yield is high and the contents of benzopyrenes are low even without processing at high pressure and high temperature.

In addition, the *Gynostemma pentaphyllum* tea or the *Gynostemma pentaphyllum* tea extract contains 0.5-14 mg/g of ginsenoside Rg3, 15-80 mg/g of gypenoside L, 10-60 mg/g of gypenoside LI, 10-20 mg/g of damulin A, 10-20 mg/g of damulin B and 10 ppb or less (e.g., 0.01-10 ppb) of benzopyrenes.

More specifically, the *Gynostemma pentaphyllum* tea or the *Gynostemma pentaphyllum* tea extract may contain 0.5-14 mg/g, specifically 2.0-7.0 mg/g, more specifically 2.0-5.0 mg/g, more specifically 2.0-4.0 mg/g, more specifically 2.5-3.5 mg/g, of ginsenoside Rg3. In addition, it may contain 15-80 mg/g, specifically 20-40 mg/g, more specifically 20-30 mg/g, more specifically 20-25 mg/g, of gypenoside L. In addition, it may contain 10-60 mg/g, specifically 10-30 mg/g, more specifically 10-20 mg/g, more specifically 10-15 mg/g, of gypenoside LI. In addition, it may contain 10-20 mg/g, specifically 10-15 mg/g, of damulin A. In addition, it may contain 10-20 mg/g, specifically 10-15 mg/g, of damulin B.

The *Gynostemma pentaphyllum* tea or the *Gynostemma pentaphyllum* tea extract may be prepared into a concentrate or a dry powder. Specifically, it may be prepared by concentrating a filtered *Gynostemma pentaphyllum* tea or *Gynostemma pentaphyllum* tea extract to 60-70 Brix. Alternatively, the *Gynostemma pentaphyllum* tea or the *Gynostemma pentaphyllum* tea extract may be prepared into a powder through an additional process such as vacuum drying, freeze-drying, spray drying, etc.

The food composition of the present disclosure includes all types including functional foods, health functional foods, nutritional supplements, health foods, food additives, etc. The food composition may be prepared into various forms according to common methods known in the art.

In the present disclosure, the food composition may be a health functional food composition.

The term "health functional food" used in the present disclosure means a food prepared and processed by using raw materials or ingredients having functionality useful for the human body according to the Health Functional Foods Act (No. 6727). The 'functional' refers to intake for the purpose of controlling nutrients for the structure and function of the human body or obtaining useful effects such as physiological effects.

The food composition of the present disclosure may contain 0.001-100 wt %, specifically 0.05-50 wt %, of the *Gynostemma pentaphyllum* tea or the *Gynostemma pentaphyllum* tea extract based on the total weight of the composition. If the content of the *Gynostemma pentaphyllum* tea or the *Gynostemma pentaphyllum* tea extract is below the above ranges, it is difficult to expect the effect of the *Gynostemma pentaphyllum* tea or the *Gynostemma pentaphyllum* tea extract.

The health functional food composition may be formulated into any one selected from a group consisting of tablet, pill, dust, granule, powder, capsule and liquid formulations by containing one or more of a carrier, a diluent, an excipient and an additive.

In addition, as specific examples of the food composition, the *Gynostemma pentaphyllum* tea or *Gynostemma pentaphyllum* tea extract of the present disclosure may be prepared into a tea, a juice, a drink, etc. for drinking. In addition, the *Gynostemma pentaphyllum* tea or *Gynostemma pentaphyllum* tea extract of the present disclosure may be prepared into a composition by mixing with a known substance or active ingredient known to have antiobesity effect. For example, the food composition of the present disclosure may further contain a trace amount of minerals, vitamins, sugars and an ingredient known to have antiobesity effect in addition to the *Gynostemma pentaphyllum* tea or the *Gynostemma pentaphyllum* tea extract.

The *Gynostemma pentaphyllum* tea or *Gynostemma pentaphyllum* tea extract of the present disclosure may be added to a food either alone or together with another food or food ingredient according to a common method. The mixing amount of the active ingredient may be determined appropriately depending on the purpose of use (for prevention or alleviation). In general, the amount of the food composition in the food may be 0.001-100 wt %, specifically 0.01-50 wt %, more specifically 0.1-30 wt %, of the total food weight. However, in the case of long-term intake for the purpose of body weight reduction and/or body fat reduction or health care, the amount may be less than the above ranges. In addition, since there is no safety issue, the active ingredient may be used in an amount exceeding the above ranges.

As described below in the examples, the *Gynostemma pentaphyllum* tea or *Gynostemma pentaphyllum* tea extract of the present disclosure has superior effect in activating AMPK and phosphorylating ACC because it contains gypenoside compounds as active ingredients. In addition, it has superior effect in promoting beta oxidation of fatty acids and promoting glucose uptake. It was confirmed that the *Gynostemma pentaphyllum* tea or *Gynostemma pentaphyllum* tea extract of the present disclosure has superior effect of reducing body weight and body fat.

In addition, the present disclosure provides a pharmaceutical composition for antiobesity, which contains a *Gynostemma pentaphyllum* tea or a *Gynostemma pentaphyllum* tea extract containing gypenoside L and gypenoside LI at a weight ratio of 100:20-80, specifically 100:30-70, more specifically 100:50-70, as an active ingredient.

In addition, the *Gynostemma pentaphyllum* tea or *Gynostemma pentaphyllum* tea extract of the present disclosure may contain the gypenoside L and the gypenoside LI at a concentration of 20-140 mg/g, specifically 25-140 mg/g, more specifically 30-120 mg/g, more specifically 30-100 mg/g, specifically 30-60 mg/g.

The pharmaceutical composition for antiobesity of the present disclosure may be used for prevention or treatment of a disease caused by obesity. Such a disease may be, for example, diabetes, hyperlipidemia, fatty liver, arteriosclerosis, hypertension, cardiovascular diseases or metabolic syndrome in which these diseases occur simultaneously.

The pharmaceutical composition may further contain a pharmaceutically acceptable carrier. The pharmaceutically acceptable carrier is commonly used in preparation and includes saline, sterile water, Ringer's solution, buffered saline, cyclodextrin, dextrose solution, maltodextrin solution, glycerol, ethanol, liposome, etc., although not being limited thereto. If necessary, the pharmaceutical composition may further contain other common additives such as an antioxidant, a buffer, etc. In addition, it may be formulated into an aqueous solvent, a suspension, an emulsion, etc. by additionally adding a diluent, a dispersant, a surfactant, a binder, a lubricant, etc. The pharmaceutical composition of the present disclosure may be formulated into an injection, a formulation for oral administration, a formulation for external application to skin, etc., although not being specially limited thereto.

The pharmaceutical composition can be administered orally or parenterally (e.g., intravenously, subcutaneously, intraperitoneally or topically) depending on the intended method. The administration dosage may be determined appropriately by those skilled in the art although it varies depending on the patient's condition and body weight, the degree of a disease, drug type, administration route and time, etc.

Additionally, the dosage level of the composition will depend on the activity of a compound, administration route, the severity of the condition being treated and the condition and medical history of a patient. However, the administration dosage can be increased gradually starting from a dosage which is lower than that required to achieve the desired therapeutic effect until the desired effect is achieved within the knowledge of the art, and the desirable administration dosage may be determined depending on age, sex, body type and body weight. The composition may be processed further before it is formulated into a pharmaceutically acceptable formulation. Specifically, it may be pulverized or ground into smaller particles. The effective dose of the *Gynostemma pentaphyllum* tea or *Gynostemma pentaphyllum* tea extract of the present disclosure to achieve the desired effect is 0.001-400 mg/kg, specifically 0.01-100 mg/kg, and it may be administered 1-3 times a day. The administration dosage does not limit the scope of the present disclosure in any way.

The pharmaceutical composition of the present disclosure can be prepared into a unit or multiple dosage form using a pharmaceutically acceptable carrier and/or excipient according to a method that can be easily performed by those having ordinary knowledge in the art to which the present disclosure belongs. The formulation may be any pharmaceutically acceptable formulation including an oral formulation such as a powder, a granule, a tablet, a capsule, a suspension, an emulsion, a syrup, an aerosol, etc., a formulation for external application such as an ointment, a cream, etc., a suppository, a sterilized injection solution, etc., and may further contain a dispersant or a stabilizer.

Hereinafter, the *Gynostemma pentaphyllum* tea or *Gynostemma pentaphyllum* tea extract according to the present disclosure will be described in detail through examples.

EXAMPLES

Example 1: Preparation of *Gynostemma Pentaphyllum* Leaf Tea Through High-Temperature Heat Treatment of Fresh *Gynostemma pentaphyllum* Leaf (1) 10 kg of fresh *Gynostemma pentaphyllum* leaf was washed with clear water and then moisture was removed (FIG. 1).

(2) Then, the *Gynostemma pentaphyllum* leaf was supplied to a double boiling container inside an electric extractor (Kyungseo Machine, COSMOS-660). After sealing and adjusting the temperature inside the electric extractor to 130° C., heating was performed for 3 hours.

(3) After the heating was completed, water vapor was discharged with a condenser by slowly opening a valve of the electric extractor (equipped with the condenser and a vacuum pump). When the internal temperature was decreased to 100° C. or lower, the *Gynostemma pentaphyllum* leaf was dried under reduced pressure by slowly operating the vacuum pump. During this process, a small amount of leachate was generated from the *Gynostemma pentaphyllum* leaf, which was absorbed again into *Gynostemma pentaphyllum* leaf tea due to evaporation by the latent heat in the device. After the temperature inside the electric extractor reached 70° C., the drying under reduced pressure was continued while maintaining the temperature at 70° C. through additional heating. When no more waster was recovered from the condenser, 2,523 g of *Gynostemma pentaphyllum* leaf with a water content of 67.5 wt % was recovered.

(4) 825 g of *Gynostemma pentaphyllum* leaf tea with a water content of 7 wt % was obtained by hot air-drying the recovered *Gynostemma pentaphyllum* leaf at 65° C.

(5) 10 g of the *Gynostemma pentaphyllum* leaf tea was ground finely with a mixer. After adding 100 mL of 70% (v/v) ethanol, the *Gynostemma pentaphyllum* leaf tea was extracted 3 times at 80° C. for 2 hours, filtered and then dried for use as a sample for analysis.

Example 2: Preparation of *Gynostemma Pentaphyllum* Leaf Tea by Heating and Drying Fresh *Gynostemma Pentaphyllum* Leaf (1) 10 kg of fresh *Gynostemma pentaphyllum* leaf was washed with clear water and then moisture was removed.

The fresh *Gynostemma pentaphyllum* leaf (water content: 91.8 wt %) was put in an open container. Then, 4,985 g of *Gynostemma pentaphyllum* leaf with a water content of 83.6 wt % was obtained without generation of a leachate by heating at 150° C. using an electric heater.

2,543 g of *Gynostemma pentaphyllum* leaf with a water content of 69.5 wt % was recovered by performing the steps (2) and (3) in the same manner as in Example 1.

829 g of *Gynostemma pentaphyllum* leaf tea with a water content of 2.9% was obtained by performing the step (4) in the same manner as in Example 1, and a sample for analysis was prepared in the same manner as in the step (5) of Example 1.

Example 3: Preparation of *Gynostemma Pentaphyllum* Leaf Tea Extract from Fresh *Gynostemma Pentaphyllum* Leaf 100 g of the *Gynostemma pentaphyllum* leaf teas obtained in the step (4) of Examples 1 and 2 were extracted at 90° C. for 4 hours by adding 1,200 mL of water and the extract was filtered with a 20-μm filter. After adding 1,200 mL of 50% v/v ethanol to the remaining residue and extracting at 80° C. for 2 hours followed by filtering, the two extracts were combined, concentrated under reduced pressure, freeze-dried and then prepared into powder, to recover 31.8 g and 30.9 g, respectively. They were used as *Gynostemma pentaphyllum* leaf tea extract samples for analysis (Example 3-1 (*Gynostemma pentaphyllum* leaf tea extract of Example 1) and Example 3-2 (*Gynostemma pentaphyllum* leaf tea extract of Example 2), respectively).

Figure 2:
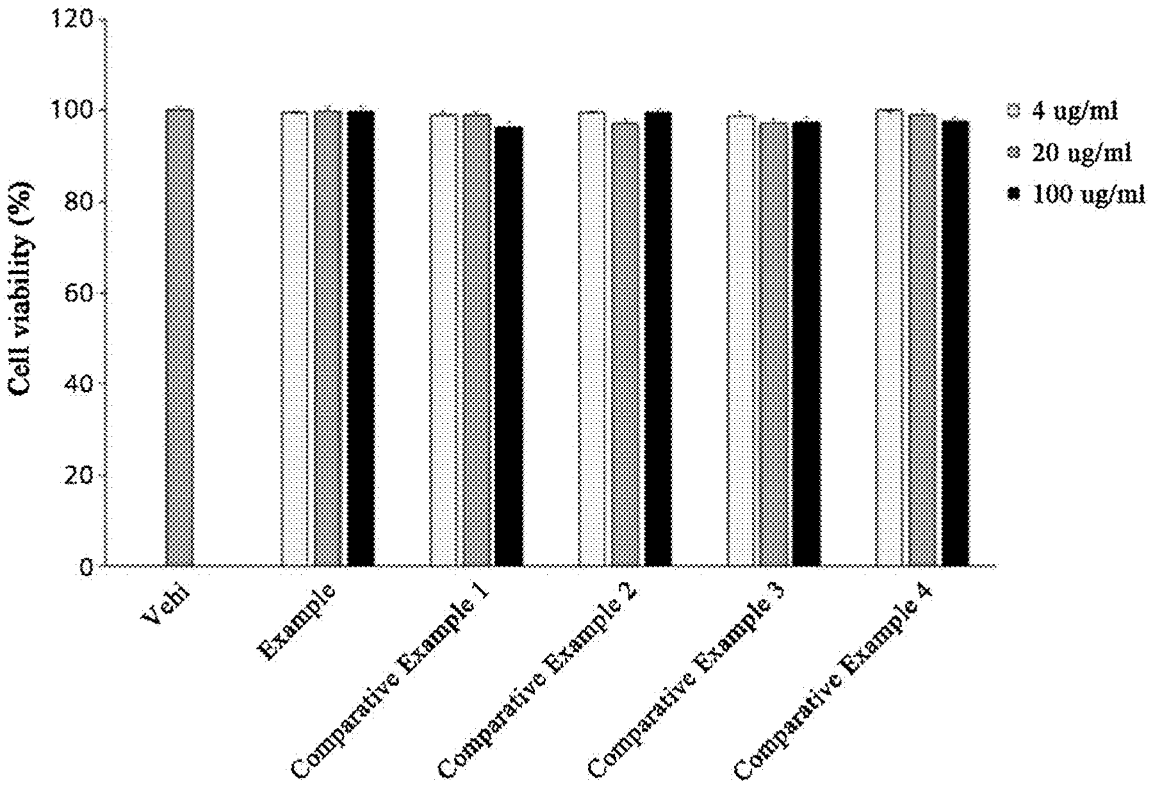
FIG. 2 shows the effect of *Gynostemma pentaphyllum* tea extracts according to an example and comparative examples of the present disclosure on cell viability.

Example 4: Preparation of *Gynostemma Pentaphyllum* Leaf Tea Through Swelling and High-Temperature Heat Treatment of Dried *Gynostemma pentaphyllum* Leaf (1) 728 g of dried *Gynostemma pentaphyllum* leaf was obtained by roasting 10 kg of fresh *Gynostemma pentaphyllum* leaf at 300° C. for 1 hour using an electric heater and then drying to a water content of 8% (FIG. 2).

100 g of the dried *Gynostemma pentaphyllum* leaf and 400 g of water was supplied to the pressurized sealed container and then sealed.

(2) The *Gynostemma pentaphyllum* leaf in the sealed container was swollen by heating the pressurized sealed container to 120° C. at a rate of 1.0° C./min (water content: 80 wt %).

(3) Then, the pressurized sealed container was heated at 120° C. for 4 hours.

(4) After stopping heating the pressurized sealed container, the sealed container was opened by releasing pressure. Then, semi-dried *Gynostemma pentaphyllum* leaf was recovered (water content: 65 wt %).

(5) 98.5 g of *Gynostemma pentaphyllum* leaf tea with a water content of 8% was obtained by hot air-drying the recovered *Gynostemma pentaphyllum* leaf at 65° C.

(6) 10 g of the *Gynostemma pentaphyllum* leaf tea was ground finely with a mixer and then, after adding 100 mL of 70% ethanol, extracted 3 times at 80° C. for 2 hours, filtered and dried for use as a *Gynostemma pentaphyllum* leaf tea sample for analysis.

Example 5: Preparation of *Gynostemma pentaphyllum* Leaf Tea Extract from Dried *Gynostemma pentaphyllum* Leaf After adding 1,500 mL of 50% v/v ethanol, 100 g of the *Gynostemma pentaphyllum* leaf tea obtained in the step (5) of Example 4 was extracted twice at 80° C. for 2 hours, concentrated under reduced pressure, freeze-dried and then prepared into powder. 31.5 g (extraction yield: 31.5%) of the recovered powder was used as a sample for analysis.

<Analysis of Low-Molecular-Weight Effective Saponin>

HPLC analysis was performed under the condition described in Table 1 in order to measure the contents of active ingredients in the *Gynostemma pentaphyllum* leaf tea or *Gynostemma pentaphyllum* leaf tea extract of Examples 1-5. The result is shown in Table 2 and Table 3.

(1) Preparation of standard stock solution: About 20 mg of standard material was weighed accurately and dissolved in 60% methanol in a 20-mL volumetric flask (stock solution: 1,000 ppm).

(2) Preparation of standard solutions: 0.3, 0.6, 1.2, 2.0 or 3.0 mL of the standard stock solution was placed in a 10-mL volumetric flask and 60% methanol was added to the marked line. The prepared solutions were used as standard solutions (30, 60, 120, 200, 300 ppm).

(3) Preparation of test solution: 500 mg of the sample was weighed and placed in a 50-mL volumetric flask. After filling half with 60% methanol, ultrasonic extraction was performed for 30 minutes. After cooling at room temperature, 60% methanol was added to the marked line. A test solution was prepared by filtering the solution with a 0.45-μm Nylon syringe filter.

(4) The instrumental analysis conditions are described in Table 1 and the analysis result is shown in Table 2 and Table 3.

As the standard materials used in the experiment, damulin A (purity: 99.1%) and damulin B (purity: 95.96%) were purchased from Chengdu Biopurify Phytochemicals (China), gypenoside L (purity: 99.42%) from Shanghai Yuanye Bio-Technology (China), gypenoside LI (purity: 99.33%) from Korea Research Institute of Bioscience & Biotechnology and ginsenoside Rg3 (purity: 98.24%) from Ambo (Korea).

TABLE 1

| | | | |
|---|---|---|---|
| Analytical instrument | HPLC-DAD | | |
| Detection wavelength | 204 nm | | |
| Column | Agilent ZORBAX Eclipse C18 (4.6 × 250 mm, 5 μm particle size) | | |
| Column temperature | 35° C. | | |
| Injection volume | 10 μL | | |
| Flow rate | 1.0 mL/min | | |
| | Solvent A : DW, Solvent B : Acetonitrile | | |
| Mobile phase | Time (min) | Solvent A (%) | Solvent B (%) |
| | 0 | 60 | 40 |
| | 20 | 60 | 40 |
| | 35 | 50 | 50 |
| | 40 | 50 | 50 |
| | 40.1 | 0 | 100 |
| | 50 | 0 | 100 |
| | 50.1 | 60 | 40 |
| | 60 | 60 | 40 |

TABLE 2

| When fresh *Gynostemma pentaphyllum* leaf was used | | | | | | |
|---|---|---|---|---|---|---|
| Unit: mg/g | Gypenoside L | Gypenoside LI | Rg3 | Damulin A | Damulin B | Benzopyrene (ppb) |
| Example 1 | 8.11 | 5.12 | 1.01 | 5.01 | 4.28 | 0.5 |
| Example 2 | 8.29 | 5.23 | 1.18 | 5.61 | 4.32 | 5.5 |
| Example 3-1 | 23.05 | 13.87 | 2.59 | 12.77 | 11.19 | 1.8 |
| Example 3-2 | 22.75 | 13.81 | 2.63 | 12.98 | 11.23 | 6.8 |

As shown in Table 2, there was no significant difference in contents between the *Gynostemma pentaphyllum* leaf tea prepared by directly heat-treating fresh leaf and the one prepared by roasting fresh *Gynostemma pentaphyllum* leaf. However, the benzopyrene content was relatively high in Example 2 due to the heat treatment during the drying process prior to the heat treatment of the fresh *Gynostemma pentaphyllum* leaf.

The *Gynostemma pentaphyllum* leaf tea extracts of Examples 3-1 and 3-2 were filtered with a 20-μm filter without an additional purification process such as centrifugation, solvent separation, column separation, etc. By controlling the size of the filter and performing adequate centrifugation, solvent separation, column separation, etc., the contents of saponins can be increased several to tens of times.

TABLE 3

| When dried *Gynostemma pentaphyllum* leaf was used | | | | | | |
|---|---|---|---|---|---|---|
| Unit: mg/g | Gypenoside L | Gypenoside LI | Rg3 | Damulin A | Damulin B | Benzopyrene (ppb) |
| Example 4 | 7.09 | 4.35 | 0.81 | 4.09 | 3.38 | 4.5 |
| Example 5 | 23.05 | 13.92 | 2.65 | 13.28 | 11.27 | 6.8 |

When comparing Table 2 and Table 3, it can be seen that the contents of low-molecular-weight effective saponins of the *Gynostemma pentaphyllum* leaf teas of the present disclosure are similar regardless of whether the fresh leaf or the roasted *Gynostemma pentaphyllum* leaf was used.

TEST EXAMPLES

Test Example 1. Change in Contents of Active Ingredients Depending on Water Supply Amount The change in the active ingredients of the *Gynostemma pentaphyllum* leaf tea extract depending on the water supply amount in the step (1) of Example 5 was investigated.

To this end, *Gynostemma pentaphyllum* leaf tea extract samples were prepared by varying the water supply amount in the step (1) of Example 5 as 0 g, 50 g, 100 g, 200 g, 300 g, 400 g (Example 4), 700 g, 1300 g and 2000 g, respectively. The contents of low-molecular-weight effective saponins contained in the samples were measured according to the method described above and the result is shown in Table 4. In addition, after the step (2) of Example 5 was completed, the *Gynostemma pentaphyllum* leaf was recovered from the sealed container and the water content in the *Gynostemma pentaphyllum* leaf was measured. The result is also shown in Table 4.

TABLE 4

| When dried *Gynostemma pentaphyllum* leaf was used (Example 5) | | | | | | | |
|---|---|---|---|---|---|---|---|
| Water supply amount | Gypenoside L (mg/g) | Gypenoside LI (mg/g) | Rg3 (mg/g) | Damulin A (mg/g) | Damulin B (mg/g) | Benzopyrene (ppb) | Water content (%) |
| 2000 g (1:20) | 16.81 | 10.01 | 1.52 | 8.33 | 6.75 | 16.8 | 94.5 |
| 1300 g (1:13) | 19.31 | 12.72 | 1.84 | 10.46 | 8.12 | 9.7 | 93 |
| 700 g (1:7) | 20.35 | 13.12 | 2.14 | 12.86 | 10.42 | 7.7 | 87.5 |
| 400 g (1:4) | 23.05 | 13.92 | 2.65 | 13.28 | 11.27 | 6.8 | 80 |
| 300 g (1:3) | 22.95 | 13.94 | 2.57 | 13.52 | 11.32 | 7.0 | 75 |
| 200 g (1:2) | 16.58 | 9.92 | 1.51 | 9.35 | 6.32 | 7.5 | 67 |
| 100 g (1:1) | 8.27 | 5.05 | 0.85 | 3.53 | 3.12 | 11.2 | 50 |
| 50 g (1:0.5) | 2.32 | 1.40 | 0.25 | 1.21 | 1.32 | 17.5 | 33 |
| 0 g | 0.00 | 0.00 | 0.00 | 0.00 | 0.00 | 28.7 | 8 |

From Table 4, it can be seen that, when water was not supplied to the dried *Gynostemma pentaphyllum* leaf of Example 5, no compositional conversion despite the heat treatment. When the weight ratio of *Gynostemma pentaphyllum* leaf and water was 1:0.5, conversion to low-molecular-weight effective saponins occurred but the conversion rate was low. The conversion to low-molecular-weight effective saponins was increased as the water supply amount was increased. In addition, when the weight ratio of *Gynostemma pentaphyllum* leaf and water was 1:2, the contents of low-molecular-weight effective saponins were increased significantly.

In particular, when the weight ratio of *Gynostemma pentaphyllum* leaf and water was 1:4 as in Example 5, the contents of low-molecular-weight effective saponins were remarkably high and the benzopyrene content was the lowest.

Meanwhile, when water was supplied in excess (weight ratio of *Gynostemma pentaphyllum* leaf and water=1:20), the contents of low-molecular-weight effective saponins were decreased due to generation of a large amount of leachate and the benzopyrene content was increased because the benzopyrenes that had been dissolved in water were absorbed again into the *Gynostemma pentaphyllum* leaf tea.

From these results, it can be seen that the *Gynostemma pentaphyllum* leaf tea prepared according to the present disclosure has significantly increased contents of low-molecular-weight effective saponins and a decreased benzopyrene content as compared to the *Gynostemma pentaphyllum* leaf tea prepared without supplying water or prepared by supplying excess water.

Test Example 2. Change in Contents of Active Ingredients Depending on Heating Temperature In order to investigate the change in the contents of active ingredients depending on the heating temperature in the step (2) of Example 3-2 and the step (3) of Example 5, the contents of active ingredients in *Gynostemma pentaphyllum* leaf tea extracts prepared by heating at 100° C., 110° C., 115° C., 121° C., 130° C. or 150° C., respectively, for 6 hours were measured. The result is shown in Table 5 and Table 6.

TABLE 5

| When fresh *Gynostemma pentaphyllum* leaf was used (Example 3-2) | | | | | |
|---|---|---|---|---|---|
| Unit: mg/g | Gypenoside L | Gypenoside LI | Rg3 | Damulin A | Damulin B |
| 100° C. | 0.00 | 0.00 | 0.00 | 0.01 | 0.00 |
| 110° C. | 0.01 | 0.09 | 0.00 | 0.01 | 0.00 |
| 115° C. | 6.71 | 4.78 | 0.98 | 4.89 | 4.21 |
| 121° C. | 24.98 | 13.82 | 2.48 | 14.91 | 11.28 |
| 130° C. | 19.45 | 12.49 | 2.13 | 12.82 | 10.47 |
| 150° C. | 17.83 | 11.21 | 2.06 | 8.82 | 6.43 |

TABLE 6

| When dried *Gynostemma pentaphyllum* leaf was used (Example 5) | | | | | |
|---|---|---|---|---|---|
| Unit: mg/g | Gypenoside L | Gypenoside LI | Rg3 | Damulin A | Damulin B |
| 100° C. | 0.11 | 0.00 | 0.00 | 0.01 | 0.00 |
| 110° C. | 0.12 | 0.09 | 0.00 | 0.01 | 0.00 |
| 115° C. | 6.69 | 4.73 | 0.94 | 4.85 | 4.52 |
| 121° C. | 22.98 | 13.52 | 2.28 | 12.95 | 10.28 |
| 130° C. | 20.45 | 13.49 | 2.83 | 12.82 | 10.47 |
| 150° C. | 17.25 | 11.31 | 2.12 | 11.52 | 9.34 |

From Table 5 and Table 6, it can be seen that there was no significant change in the contents of low-molecular-weight effective saponins contained in the *Gynostemma pentaphyllum* leaf when the heating temperature was 100° C. or 110° C. and there was significant change when the temperature was 115° C. or higher. Therefore, it is thought that the critical temperature is between 110 and 115° C. Meanwhile, the contents of low-molecular-weight effective saponins reached peaks at 121° C. and decreased slowly as the temperature was increased further. Because the heating temperature and heating time are inversely proportional to each other, a shorter heating time is required if the heating temperature is increased. It is thought that the active ingredients were degraded when the heating time was too long.

From these results, it can be seen that the contents of low-molecular-weight effective saponins in the *Gynostemma pentaphyllum* leaf tea prepared according to the present disclosure are increased significantly as compared to the *Gynostemma pentaphyllum* leaf tea prepared by heating at 110° C. or lower. In particular, it can be seen that the contents of low-molecular-weight effective saponins are high when the *Gynostemma pentaphyllum* leaf tea according to the present disclosure is prepared by heating at specifically 120-150° C., more specifically 120-130° C., more specifically 121-130° C.

Test Example 3. Change in Contents of Active Ingredients Depending on Heating Time In order to investigate the change in the contents of active ingredients depending on the heating time in the step (2) of Example 3-2 and the step (3) of Example 5, the contents of active ingredients in *Gynostemma pentaphyllum* leaf tea extracts prepared by heating at 130° C. for 0, 1, 2, 3, 4, 6, 8, 12 or 24 hours, respectively, were measured. The result is shown in Table 7 and Table 8.

TABLE 7

| When fresh *Gynostemma pentaphyllum* leaf was used (Example 3-2) | | | | | | |
|---|---|---|---|---|---|---|
| Unit: mg/g | Gypenoside L | Gypenoside LI | Rg3 | Damulin A | Damulin B | Benzopyrene (ppb) |
| 0 hours | 0.00 | 0.00 | 0.00 | 0.00 | 0.00 | 0.45 |
| 1 hour | 8.55 | 5.47 | 1.21 | 5.27 | 4.83 | 0.49 |
| 2 hours | 18.65 | 14.15 | 2.15 | 10.53 | 8.48 | 0.82 |
| 3 hours | 25.05 | 13.92 | 2.65 | 15.05 | 11.42 | 1.71 |
| 4 hours | 22.05 | 12.32 | 2.35 | 12.01 | 9.42 | 2.74 |
| 6 hours | 19.45 | 12.49 | 2.13 | 12.82 | 10.47 | 2.82 |
| 8 hours | 18.20 | 11.16 | 1.23 | 10.15 | 8.14 | 3.65 |
| 12 hours | 16.03 | 9.23 | 1.09 | 8.41 | 6.33 | 4.83 |
| 24 hours | 14.35 | 8.72 | 1.08 | 6.31 | 4.34 | 9.31 |

TABLE 8

| When *Gynostemma pentaphyllum* leaf dried by roasting was used (Example 5) | | | | | | |
|---|---|---|---|---|---|---|
| Unit: mg/g | Gypenoside L | Gypenoside LI | Rg3 | Damulin A | Damulin B | Benzopyrene (ppb) |
| 0 hours | 0.00 | 0.00 | 0.00 | 0.00 | 0.00 | 25.7 |
| 1 hour | 4.25 | 3.28 | 0.52 | 3.12 | 2.75 | 19.3 |
| 2 hours | 8.45 | 6.95 | 1.20 | 6.23 | 5.28 | 12.8 |
| 3 hours | 20.45 | 13.49 | 2.83 | 12.82 | 13.47 | 9.5 |
| 4 hours | 23.05 | 13.92 | 2.65 | 13.28 | 11.27 | 6.8 |
| 6 hours | 22.98 | 13.52 | 2.28 | 12.95 | 10.28 | 7.2 |
| 8 hours | 20.21 | 13.28 | 1.92 | 12.33 | 9.82 | 8.6 |
| 12 hours | 18.23 | 11.32 | 1.01 | 9.58 | 7.52 | 9.8 |
| 24 hours | 15.35 | 8.89 | 0.92 | 7.52 | 5.99 | 11.3 |

From Table 7, it can be seen that the contents of low-molecular-weight effective saponins in the *Gynostemma pentaphyllum* leaf tea according to the present disclosure began to increase from 1 hour after the heating in the step (2) and increased significantly from 2 hours. They reached peaks at 3-4 hours and then decreased slowly after 6 hours.

In addition, from Table 8, it can be seen that the contents of low-molecular-weight effective saponins of the *Gynostemma pentaphyllum* leaf tea according to the present disclosure began to increase from 1 hour after the heating in the step (3) and increased significantly from 3 hours. They reached peaks at 4-6 hours and then decreased slowly after 6 hours.

It is though that the decrease of the contents of low-molecular-weight effective saponins with increasing heating time is because the low-molecular-weight effective saponins were converted to smaller molecules or degraded due to the heating for a long time.

It was confirmed that the *Gynostemma pentaphyllum* leaf tea contains low-molecular-weight effective saponins at high contents when it is heated in the step (2) or the step (3) for 2-12 hours, specifically 2-8 hours, more specifically 3-8 hours, more specifically 3-6 hours, more specifically 4-6 hours, more specifically 3-4 hours, most specifically 4 hours.

Meanwhile, the contents of benzopyrenes were increased with heating time.

Comparative Example 1: Natural Drying—General Extraction

Dried *Gynostemma pentaphyllum* leaf was obtained by spreading fresh *Gynostemma pentaphyllum* leaf and naturally drying the same in the shade to a water content of 8%.

The dried *Gynostemma pentaphyllum* leaf was prepared into a *Gynostemma pentaphyllum* leaf tea extract by extracting twice at with ethanol (50% v/v) of 15 volume equivalents, which was concentrated under reduced pressure, freeze-dried and prepared into powder for use as a sample for analysis.

Comparative Example 2-1: Natural Drying—General Extraction—Heat Treatment (1)

The extract of Comparative Example 1 was added to 2 volume equivalents of purified water, suspended by stirring enough, heat-treated at 120° C. for 2 hours using a sterilizer, dried and prepared into powder for use as a sample for analysis.

Comparative Example 2-2: Natural Drying—General Extraction—Heat Treatment (2)

Dried *Gynostemma pentaphyllum* leaf was obtained by spreading fresh *Gynostemma pentaphyllum* leaf and naturally drying the same in the shade to a water content of 7%.

A *Gynostemma pentaphyllum* leaf tea extract was prepared by extracting the dried *Gynostemma pentaphyllum* leaf twice at 80° C. with ethanol (50% v/v) of 15 weight equivalents.

The *Gynostemma pentaphyllum* leaf extract was concentrated to a solid content of 22 wt % and then heated at 121° C. for 4 hours.

The heated *Gynostemma pentaphyllum* leaf extract was concentrated under reduced pressure, freeze-dried and then prepared into powder for use as a *Gynostemma pentaphyllum* leaf tea extract sample for analysis.

Comparative Example 3: Natural Drying—Swelling—High-Temperature Heat Treatment—General Extraction The experimental procedure was the same as in Example 5 except that *Gynostemma pentaphyllum* leaf naturally dried in the shade was used in the step (1) instead of the *Gynostemma pentaphyllum* leaf dried after roasting.

Comparative Example 4-1: Drying after Roasting—General Extraction (1)

Dried *Gynostemma pentaphyllum* leaf was prepared by roasting fresh *Gynostemma pentaphyllum* leaf at 150° C. using an electric heater and then drying to a water content of 8%.

The dried *Gynostemma pentaphyllum* leaf was extracted twice at 80° C. with ethanol (50% v/v) of 15 volume equivalents. The prepared *Gynostemma pentaphyllum* leaf tea extract was concentrated under reduced pressure, freeze-dried and prepared into powder for use as a sample for analysis. The ethanol extraction yield of the roasted *Gynostemma pentaphyllum* leaf was 20.4% on average.

Comparative Example 4-2: Drying after Roasting—General Extraction (2)

*Gynostemma pentaphyllum* leaf tea was prepared by roasting fresh *Gynostemma pentaphyllum* leaf at 130° C. for 30 minutes using an electric heater and then drying to a water content of 7%.

The *Gynostemma pentaphyllum* leaf tea was extracted twice at 80° C. with ethanol (50% v/v) of 15 volume equivalents. The prepared *Gynostemma pentaphyllum* leaf tea extract was concentrated under reduced pressure, freeze-dried and prepared into powder for use as a sample for analysis.

Comparative Example 5: Drying after Roasting—High-Temperature Dry Heat Treatment—General Extraction Dried *Gynostemma pentaphyllum* leaf was prepared by roasting fresh *Gynostemma pentaphyllum* leaf at 150° C. using an electric heater and then drying to a water content of 8%.

The dried *Gynostemma pentaphyllum* leaf was placed in a sterilizer and heated at 120° C. for 4 hours (dry heat treatment).

The heat-treated *Gynostemma pentaphyllum* leaf was extracted twice at 80° C. with ethanol (50% v/v) of 15 volume equivalents. The prepared *Gynostemma pentaphyllum* leaf tea extract was concentrated under reduced pressure, freeze-dried and prepared into powder for use as a sample for analysis.

Comparative Example 6: Drying after Roasting—High-Temperature Extraction

Dried *Gynostemma pentaphyllum* leaf was prepared by roasting fresh *Gynostemma pentaphyllum* leaf at 150° C. using an electric heater and then drying to a water content of 8%.

A *Gynostemma pentaphyllum* leaf hot water extract was prepared by adding 15 volume equivalents of water to the dried *Gynostemma pentaphyllum* leaf and conducting hot water extraction at 120° C. for 2 hours. Then, a *Gynostemma*

*pentaphyllum* leaf ethanol extract was prepared by extracting the remaining residue at 80° C. with ethanol (50% v/v) of 15 volume equivalents. The extraction yield was 36.8%. After mixing the *Gynostemma pentaphyllum* leaf hot water extract and ethanol extract, the mixture was concentrated under reduced pressure, freeze-dried and prepared into powder for use as a sample for analysis.

Comparative Example 7-1: Drying after Roasting—General Extraction—Heat Treatment (1)

The extract of Comparative Example 4-1 was suspended by stirring enough after adding 2 volume equivalents of purified water, heat-treated at 120° C. for 2 hours using a sterilizer, dried and prepared into powder for use as a sample for analysis.

Comparative Example 7-2: Drying after Roasting—General Extraction—Heat Treatment (2)

*Gynostemma pentaphyllum* leaf tea was prepared by roasting fresh *Gynostemma pentaphyllum* leaf at 130° C. for 30 minutes using an electric heater and then drying to a water content of 7%.

A *Gynostemma pentaphyllum* leaf tea extract was prepared by extracting the *Gynostemma pentaphyllum* leaf tea twice at 80° C. with ethanol (50% v/v) of 15 weight equivalents.

The *Gynostemma pentaphyllum* leaf extract was concentrated to a solid content of 22 wt % and then heated at 121° C. for 14 hours.

The heated *Gynostemma pentaphyllum* leaf extract was concentrated under reduced pressure, freeze-dried and then prepared into powder for use as a *Gynostemma pentaphyllum* leaf tea extract sample for analysis.

Test Example 4. Analysis of Contents of Active Ingredients of *Gynostemma pentaphyllum* Leaf Tea Depending on Preparation Method The contents of low-molecular-weight effective saponins contained in the samples for analysis of Example 3-2, Example 5 and Comparative Example 1-7 were measured according to the same method as in Test Example 1. The result is shown in Table 9 and Table 10.

TABLE 9

| Unit: mg/g | Gypenoside L | Gypenoside LI | Rg3 | Damulin A | Damulin B | Benzopyrene (ppb) |
|---|---|---|---|---|---|---|
| Example 3-2 | 22.75 | 13.81 | 2.63 | 12.98 | 11.23 | 1.8 |
| Comparative Example 1 | 0.00 | 0.00 | 0.00 | 0.00 | 0.00 | 1.2 |
| Comparative Example 4-2 | 1.3 | 0.9 | 0.1 | 0.7 | 0.5 | 21.5 |
| Comparative Example 2-2 | 6.3 | 4.2 | 0.3 | 2.3 | 1.8 | 10.5 |
| Comparative Example 7-2 | 18.2 | 14.3 | 1.6 | 8.2 | 6.1 | 23.5 |

From Table 9, it was confirmed that the *Gynostemma pentaphyllum* leaf tea extract of Example 3-2 according to the present disclosure has significantly higher contents of low-molecular-weight effective saponins and lower benzopyrene content as compared to Comparative Example 1, Comparative Example 4-2, Comparative Example 2-2 and Comparative Example 7-2.

Specifically, in the case of Comparative Example 1 wherein natural drying was performed without heat treatment, the contents of low-molecular-weight effective saponins were below detection limits or very low. In addition, in the case of Comparative Example 2-2 wherein the naturally dried *Gynostemma pentaphyllum* leaf tea extract was heat-treated, the contents of low-molecular-weight effective saponins were low, presumably because the effective saponins were lost due to enzymatic actions during natural drying.

In addition, the contents of low-molecular-weight saponins of the *Gynostemma pentaphyllum* leaf tea extract of Example 3-2 according to the present disclosure were significantly higher as compared to Comparative Example 7-2 and it also exhibited a much lower benzopyrene content.

TABLE 10

| Unit: mg/g | Gypenoside L | Gypenoside LI | Rg3 | Damulin A | Damulin B | Benzopyrene (ppb) |
|---|---|---|---|---|---|---|
| Example 5 | 23.05 | 13.92 | 2.65 | 13.28 | 11.27 | 6.80 |
| Comparative Example 1 | 0.00 | 0.00 | 0.00 | 0.00 | 0.00 | 1.21 |

TABLE 10-continued

| Unit: mg/g | Gypenoside L | Gypenoside LI | Rg3 | Damulin A | Damulin B | Benzopyrene (ppb) |
|---|---|---|---|---|---|---|
| Comparative Example 2-1 | 0.00 | 0.00 | 0.00 | 0.00 | 0.00 | 1.03 |
| Comparative Example 3 | 4.48 | 4.03 | 1.21 | 3.00 | 4.48 | 2.53 |
| Comparative Example 4-1 | 0.17 | 0.05 | 0.03 | 0.00 | 0.00 | 25.66 |
| Comparative Example 5 | 0.39 | 0.00 | 0.09 | 0.00 | 0.00 | 15.65 |
| Comparative Example 6 | 14.02 | 11.28 | 1.21 | 9.82 | 7.62 | 12.56 |
| Comparative Example 7-1 | 14.44 | 11.52 | 1.19 | 10.53 | 8.01 | 16.53 |

From Table 10, it was confirmed that the *Gynostemma pentaphyllum* leaf tea of Example 5 according to the present disclosure (or *Gynostemma pentaphyllum* leaf tea extract using the same) exhibits significantly higher contents of low-molecular-weight effective saponins and significantly lower benzopyrene content as compared to Comparative Example 4-7 wherein *Gynostemma pentaphyllum* leaf dried after roasting was added but heating after water supply (swelling) was not performed.

Meanwhile, in the case of Comparative Example 1-3 wherein *Gynostemma pentaphyllum* leaf naturally dried without roasting was used, the contents of low-molecular-weight effective saponins were below detection limits or very low.

Test Example 5. Accelerated Stability Test

Accelerated stability test was conducted for the *Gynostemma pentaphyllum* leaf tea powder and the *Gynostemma pentaphyllum* leaf tea extract powder according to the present disclosure.

First, the *Gynostemma pentaphyllum* leaf teas obtained in the step (4) of Example 2 and the step (5) of Example 4 were respectively ground to 200 mesh or smaller. After putting 2 g each in an aluminum foil bag, it was sealed. The bags holding the samples were stored under the condition of 40° C. and 70% relative humidity for 0, 1, 2, 3, 4, 6, 8 or 12 months, respectively. At each period, the contents of active ingredients in the *Gynostemma pentaphyllum* leaf tea were analyzed.

In addition, the *Gynostemma pentaphyllum* leaf tea extract powders of Example 3-2 and Example 5 were also stored in the same manner and the contents of active ingredients were measured.

The accelerated stability test result for the *Gynostemma pentaphyllum* leaf tea powder and the *Gynostemma pentaphyllum* leaf tea extract powder is shown in Table 11. In Table 11, the total contents of five low-molecular-weight effective saponins (ginsenoside Rg3, gypenoside L, gypenoside LI, damulin A and damulin B) contained in the *Gynostemma pentaphyllum* leaf tea powder or the *Gynostemma pentaphyllum* leaf tea extract powder are represented as relative ratios (%) of the initial values.

TABLE 11

| Storage period | Example 2 (%) *Gynostemma pentaphyllum* leaf tea (fresh *Gynostemma pentaphyllum* leaf) | Example 3-2 (%) *Gynostemma pentaphyllum* leaf tea extract (fresh *Gynostemma pentaphyllum* leaf) |
|---|---|---|
| 0 month | 100 | 100 |
| 1 month | 100.02 | 99.89 |
| 2 months | 99.92 | 99.15 |
| 3 months | 99.13 | 98.19 |
| 4 months | 98.97 | 97.38 |
| 6 months | 98.34 | 96.61 |
| 8 months | 98.11 | 94.26 |
| 12 months | 98.07 | 91.37 |

As seen from Table 11, both the *Gynostemma pentaphyllum* leaf tea powder of Example 2 and the *Gynostemma pentaphyllum* leaf tea extract powder of Example 3-2 according to the present disclosure maintained the contents of low-molecular-weight effective saponins at 90% or higher for 12 months under the accelerated test conditions. In addition, the *Gynostemma pentaphyllum* leaf tea showed very slow change in the contents of active ingredients as compared to the *Gynostemma pentaphyllum* leaf tea extract.

Test Examples

All experiments were repeated 3 times and the analysis results were expressed as mean±SEM. The results were analyzed using the GraphPad Prism 5.0 program (GraphPad Software). The difference in the test material-treated groups and the control group were analyzed by Student's t-test and one-way analysis variance (ANOVA). $P<0.05$ was considered statistically significant. In the respective data, *,  and * indicates significant difference as compared to the control group or normal group with $p<0.05$, $p<0.01$ and $p<0.001$, respectively (Student's t-test).

<In-Vitro Tests>

<Materials and Methods>

Test Materials

All test materials were provided by BTC.

Cell Culturing and Induction of Differentiation

L6 myotube cells derived from mouse skeletal muscle were purchased from American Type Culture Collection (ATCC). The L6 cells were cultured in a humidified $CO_2$ incubator (5% $CO_2$/95% air) at 37° C. using Dulbecco's modified Eagle's medium (DMEM) supplemented with 10% fetal bovine serum (FBS), 100 units/mL penicillin and 100 μg/mL streptomycin. When the cells filled about 80% of the culture dish, the cell monolayer was washed with phosphate-buffered saline (PBS, pH 7.4). Then, the cells were detached by adding trypsin-2.65 mM EDTA and subcultured while exchanging the medium every 2 days.

When the L6 cells filled about 90% of the culture dish, the cells were cultured after replacing the medium with DMEM supplemented with 2% horse serum (Gibco-Thermo Fisher Scientific) as a myocyte differentiation medium in order to induce differentiation into myocytes. The myocyte differentiation medium was exchanged every 2 days.

Test Example 6: Cytotoxicity Test

In order to investigate the cytotoxicity of the *Gynostemma pentaphyllum* tea extracts according to the examples and comparative examples, mouse L6 myotube cells were treated with the *Gynostemma pentaphyllum* tea extracts according to the examples and comparative examples at different concentrations and MTT assay was performed 24 hours later (FIG. 2). The *Gynostemma pentaphyllum* tea extract used in Test Examples 5-10 is the *Gynostemma pentaphyllum* leaf tea extract prepared in Example 3-2.

From FIG. 2, it can be seen that the treatment with the *Gynostemma pentaphyllum* tea extracts according to the examples and comparative examples has no significant effect on the proliferation of cells.

Through this, it was confirmed that the *Gynostemma pentaphyllum* tea extract of the present disclosure has no cytotoxicity.

Test Example 7: Effect on Increased AMPK Phosphorylation

ACC (acetyl-CoA carboxylase) is an important enzyme that regulates lipid metabolism in liver and muscle tissues. This enzyme carboxylates acetyl-CoA to produce malonyl-CoA. Malonyl-CoA is the most important factor that regulates the beta oxidation of fatty acids in mitochondria. If the concentration of malonyl-CoA increases, the activity of CPT-1 (carnitine palmitoyl-CoA transferase) in the mitochondrial membrane decreases, leading to inhibited beta oxidation of fatty acids. Conversely, if the concentration malonyl-CoA decreases, the beta oxidation increases and body fat reduction is promoted. The ACC is a downstream target protein of AMPK activation. When AMPK is activated, the inactivation of the ACC enzyme is promoted due to phosphorylation. As a result, the concentration of malonyl-CoA is decreased, leading to increased activity of CPT-1 in the mitochondrial membrane and increased beta oxidation of fatty acids.

In this regard, the effect of the *Gynostemma pentaphyllum* tea extracts of the examples and comparative examples on the increased phosphorylation of AMPK and ACC, the downstream target protein thereof, was investigated.

Specifically, differentiated L6 myotube cells were treated for 2 hours with each of the *Gynostemma pentaphyllum* tea extracts according to the examples and comparative examples and the degree of increased phosphorylation of the 172nd threonine residue of the AMPK α subunit and the 79th serine residue of the ACC enzyme protein was confirmed by western blot analysis according to Hwang et al.'s method (Hwang et al., *Biochem. Biophys. Res. Commun.* 371, 289-293, 2008). Based on the western blot analysis result, the activity of each protein was calculated from the ratio of each activated protein. The result is shown in Table 3.

TABLE 3

| | p-AMPK/AMPK ratio | p-ACC/ACC ratio |
|---|---|---|
| Control group | 1.00 ± 0.00 | 1.00 ± 0.00 |
| Example | 1.40 ± 0.05** | 1.35 ± 0.08** |
| Comparative Example 1 | 0.67 ± 0.10 | 0.72 ± 0.09 |
| Comparative Example 2 | 0.59 ± 0.12 | 0.68 ± 0.13 |
| Comparative Example 3 | 0.58 ± 0.08 | 0.76 ± 0.12 |
| Comparative Example 4 | 1.22 ± 0.09* | 1.24 ± 0.09* |

From Table 3, it can be seen that the phosphorylation of AMPK and ACC was increased significantly when the cells were treated with the *Gynostemma pentaphyllum* tea extract of the example as compared to the control group or treatment with the *Gynostemma pentaphyllum* tea extracts of the comparative examples.

Through these results, it can be seen that the *Gynostemma pentaphyllum* tea extract of the present disclosure has the effect of reducing body fat by increasing the beta oxidation of fatty acids.

Test Example 8: Effect on Promotion of Beta Oxidation of Fatty Acids

After treating cultured L6 myocytes with the *Gynostemma pentaphyllum* tea extracts according to the examples and comparative examples according to Hwang et al.'s method (Hwang et al., *Biochem. Biophys. Res. Commun.* 377, 1253-1258), the effect on promotion of the beta oxidation of fatty acids was investigated.

As a result, significant increase of beta oxidation was observed when the cells were treated with the *Gynostemma pentaphyllum* tea extract according to the present disclosure as shown in Table 4.

TABLE 4

| | Beta oxidation (% of control group) |
|---|---|
| Control group | 100 |
| Example | 188.2 ± 3.10*** |
| Comparative Example 1 | 114.6 ± 5.21 |
| Comparative Example 2 | 123.7 ± 4.63 |
| Comparative Example 3 | 132.3 ± 6.40 |
| Comparative Example 4 | 145.0 ± 2.00* |

Test Example 2: Effect on Promotion of Glucose Uptake

L6 myocytes were treated with the *Gynostemma pentaphyllum* tea extracts according to the examples and comparative examples and their effect on cellular glucose uptake was investigated. After adding high-concentration glucose and 2-DG (2-deoxy-[3H]D-glucose), which is not degraded in cells, to cultured L6 myocytes according to Hwang et al.'s method (Hwang et al., Biochem. Biophys. Res. Commun. 377, 1253-1258), the promotion of the cellular uptake of 2-DG by the addition of the *Gynostemma pentaphyllum* tea was investigated. The result is shown in Table 5.

TABLE 5

| | Glucose uptake (% of control group) |
|---|---|
| Control group | 1.00 |
| Example | 2.00 ± 0.07*** |
| Comparative Example 1 | 1.11 ± 0.12 |
| Comparative Example 2 | 1.55 ± 0.05* |

TABLE 5-continued

| | Glucose uptake (% of control group) |
|---|---|
| Comparative Example 3 | 1.26 ± 0.04 |
| Comparative Example 4 | 1.44 ± 0.07* |

From Table 5, it can be seen that the glucose uptake ability was increased significantly in the cells treated with the *Gynostemma pentaphyllum* tea extract according to the present disclosure.

From these results, it can be seen that the *Gynostemma pentaphyllum* tea or *Gynostemma pentaphyllum* tea extract according to the present disclosure exhibits superior antidiabetic effect by lowering blood sugar.

<In-Vivo Test>

Test Example 10: Effect on Body Fat and Body Weight Reduction 10-1: Preparation of Experimental Animals As experimental animals, 4-week-old male ICR mice were purchased from Orient Bio and acclimated for a week. Each group consisted of 10 animals. For a normal diet group (G1) and high-fat diet groups (G2 to G6), normal feed (energy ratio (kcal %); protein:carbohydrate:fat=20:70:10) or high-fat feed (energy ratio (kcal %); protein:carbohydrate:fat=20:20:60) purchased from Research Diets, Inc. (New Brunswick, NJ, USA) was provided, respectively. The feed and water were allowed freely. The specific compositions of the normal feed and the high-fat feed are described in Table 6. The test substance was administered orally at regular intervals for 8 weeks by dissolving in physiological saline (G3 to G6). For G1 and G2, physiological saline containing no test substance was administered orally. The experimental animal breeding room was maintained at 12-hour lighting cycles under the condition of 23±3° C., 50 t 10% relative humidity and 10-15 ventilations/hour. The animal experiment was conducted in accordance with the regulations of the Hallym University Institutional Animal Care and Use Committee (Hallym 2018-31).

TABLE 6

| | Normal feed (10 kcal % fat) | | High-fat feed (60 kcal % fat) | |
|---|---|---|---|---|
| | g | kcal | g | kcal |
| Casein, 80 Mesh | 200 | 800 | 200 | 800 |
| L-Cystine | 3 | 12 | 3 | 12 |
| Cornstarch | 315 | 1,260 | 0 | 0 |
| Maltodextrin 10 | 35 | 140 | 125 | 500 |
| Sucrose | 350 | 1,400 | 68.8 | 275 |
| Soybean oil | 50 | 0 | 50 | 0 |
| Lard* | 25 | 225 | 25 | 225 |
| Mineral mix | 20 | 180 | 245 | 2,205 |
| Dicalcium phosphate | 10 | 0 | 10 | 0 |
| Calcium carbonate | 13 | 0 | 13 | 0 |

TABLE 6-continued

| | Normal feed (10 kcal % fat) | | High-fat feed (60 kcal % fat) | |
|---|---|---|---|---|
| | g | kcal | g | kcal |
| Calcium carbonate | 5.5 | 0 | 5.5 | 0 |
| Potassium citrate, $1H_2O$ | 16.5 | 0 | 16.5 | 0 |
| Vitamin mix | 10 | 40 | 10 | 40 |
| Choline bitartrate | 2 | 0 | 2 | 0 |
| Total | 1,055 | 4,057 | 773.8 | 4,057 |

*Typical analysis of cholesterol in lard = 0.95 mg/g 10-2: Composition of Test Groups The experimental animals were divided into eight groups: normal group (G) to which normal feed was given for 6 weeks; control group (G2) to which high-fat feed was given; G3 to which high-fat feed was given and 300 mg/kg of the *Gynostemma pentaphyllum* tea extract of Example was administered; G4 to which 300 mg/kg of the *Gynostemma pentaphyllum* tea extract of Comparative Example was administered; G5 to which 300 mg/kg of the *Gynostemma pentaphyllum* tea extract of Comparative Example 2 was administered; G6 to which 300 mg/kg of the *Gynostemma pentaphyllum* tea extract of Comparative Example 3 was administered; G7 to which 300 mg/kg of the *Gynostemma pentaphyllum* tea extract of Comparative Example 4 was administered; and G8 to which 30 mg/kg of orlistat, which is a lipase inhibitor, was administered as a positive control group. The composition of the test groups is described specifically in Table 7.

TABLE 7

| Test groups | Feed | Sample | Sample administration dosage |
|---|---|---|---|
| G1 | Normal feed | — | — |
| G2 | High-fat feed | — | — |
| G3 | High-fat feed | Example | 300 mg/kg |
| G4 | High-fat feed | Comparative Example 1 | 300 mg/kg |
| G5 | High-fat feed | Comparative Example 2 | 300 mg/kg |
| G6 | High-fat feed | Comparative Example 3 | 300 mg/kg |
| G7 | High-fat feed | Comparative Example 4 | 300 mg/kg |
| G8 | High-fat feed | Orlistat | 30 mg/kg |

10-3: Change in Body Weight and Body Fat

Initial body weight, final body weight, total body weight gain, feed intake, body fat percentage and feed efficiency ratio (FER) were measured while providing the feed specified in 6-2 to each test group for 8 weeks. Specifically, the body weight was measured using a digital scale once a week at the same time. The feed efficiency ratio (FER) was calculated by the following equation. The result of investigating the initial body weight, final body weight, total body weight gain, feed intake, body fat percentage and feed efficiency ratio for 8 weeks is given in Table 8.

Feed efficiency ratio (FER)=body weight gain (g)/feed intake (g) [Equation]

TABLE 8

| | Initial body weight (g) | Final body weight (g) | Total body weight gain (g) | Body weight gain (%) | Total feed intake (g) | Body fat percentage (%) | Feed efficiency ratio (FER) |
|---|---|---|---|---|---|---|---|
| G1 | 21.4 ± 0.2 | 30.1 ± 0.3 | 8.7 ± 0.4 | 40.65 | 150.5 ± 0.7 | 27.4 ± 1.7 | 0.058 ± 0.002 |
| G2 | 21.5 ± 0.3 | 45.6 ± 0.6 | 24.1 ± 0.4 | 112.09 | 130.6 ± 1.4 | 43.3 ± 0.2 | 0.184 ± 0.003 |
| G3 (Example) | 21.7 ± 0.3 | 32.3 ± 0.4** | 10.6 ± 0.4** | 48.85** | 115.8 ± 1.0* | 33.8 ± 0.4** | 0.092 ± 0.004** |

TABLE 8-continued

| | Initial body weight (g) | Final body weight (g) | Total body weight gain (g) | Body weight gain (%) | Total feed intake (g) | Body fat percentage (%) | Feed efficiency ratio (FER) |
|---|---|---|---|---|---|---|---|
| G4 | 21.5 ± 0.2 | 42.3 ± 0.7 | 20.8 ± 0.5* | 96.74 | 118.1 ± 1.0 | 43.5 ± 0.4 | 0.176 ± 0.006 |
| G5 | 21.5 ± 0.2 | 41.8 ± 0.6 | 20.3 ± 0.7* | 94.42 | 121.4 ± 0.3 | 41.8 ± 0.4 | 0.167 ± 0.005 |
| G6 | 21.5 ± 0.2 | 41.5 ± 0.4 | 20.0 ± 0.6* | 93.02 | 122.1 ± 0.4 | 41.6 ± 0.6 | 0.164 ± 0.006 |
| G7 | 21.6 ± 0.3 | 38.4 ± 0.5* | 16.8 ± 0.3* | 77.78* | 119.6 ± 0.4 | 39.5 ± 0.8 | 0.140 ± 0.003 |
| G8 | 21.7 ± 0.2 | 37.1 ± 0.6* | 15.4 ± 0.2* | 70.97* | 122.4 ± 0.3 | 36.6 ± 0.7* | 0.126 ± 0.005* |

In Table 8,

*, and *indicate significant difference as compared to the control group (G2) with $p < 0.05$, $p < 0.01$ and $p < 0.001$, respectively.

From Table 8, it can be seen that the G3 test group to which the *Gynostemma pentaphyllum* tea extract of Example was administered exhibits significantly lower final body weight, total body weight gain, body weight gain percentage, body fat percentage and feed efficiency ratio as compared to the G2 test group, which is a high-fat feed control group, and the G4-G7 test groups to which the *Gynostemma pentaphyllum* tea extracts of Comparative Examples were administered. In addition, the G3 test group to which the *Gynostemma pentaphyllum* tea extract of Example was administered showed significantly lower final body weight, total body weight gain, body weight percentage, body fat percentage and feed efficiency ratio as compared to the G8 test group, which is a positive control group. Meanwhile, the G7 test group showed significant effect of suppressing body weight gain but showed no significant effect of suppressing the increase of body fat percentage.

PREPARATION EXAMPLES

Preparation Example 1: Preparation of Tablet 10 mg of the *Gynostemma pentaphyllum* tea extract powder according to the present disclosure was mixed with 9 mg of vitamin E, 9 mg of vitamin C, 200 mg of galactooligosaccharide, 60 mg of lactose and 140 mg of maltose and then granulated using a fluidized-bed dryer. After adding 6 mg of sugar ester, 500 mg of the resulting composition was prepared into a tablet according to a common method.

Preparation Example 2: Preparation of Capsule

According to a common soft capsule preparation method, 10 mg of the *Gynostemma pentaphyllum* tea extract powder according to the present disclosure was mixed with 9 mg of vitamin C, 2 mg of palm oil, 8 mg of hydrogenated vegetable oil, 4 mg of yellow beeswax and 9 mg of lecithin and then filled in a gelatin capsule.

Preparation Example 3: Preparation of Pill

The *Gynostemma pentaphyllum* tea extract according to the present disclosure was ground and passed through a 200-mesh sieve. 5 mg of the obtained *Gynostemma pentaphyllum* leaf extract powder was mixed appropriately with honey, dextrin, starch, microcrystalline cellulose, CMC calcium, etc. and then prepared into a pill.

Preparation Example 4: Preparation of Drink 20 mg of the *Gynostemma pentaphyllum* tea extract according to the present disclosure was mixed with 9 mg of vitamin E, 9 mg of vitamin C, 10 g of glucose, 0.6 g of citric acid and 25 g of oligosaccharide syrup. Then, after adding 300 mL of purified water, 200 mL of the resulting solution was filled in each bottle. Then, a drink was prepared by sterilizing at 130° C. for 4-5 seconds.

Preparation Example 5: Preparation of Granule 5 mg of the *Gynostemma pentaphyllum* tea extract according to the present disclosure was mixed with 9 mg of vitamin E, 9 mg of vitamin C, 250 mg anhydrous crystalline glucose and 550 mg of starch. After forming the mixture into granules using a fluidized-bed granulator, the granules were filled in a pouch.

Preparation Example 6: Preparation of Concentrated Liquid Tea

The *Gynostemma pentaphyllum* tea extract powder according to the present disclosure was mixed to a solid content of 15% by adding water. After heating at 90° C., 10 parts by weight of γ-cyclodextrin was added based on 100 parts by weight of the *Gynostemma pentaphyllum* tea powder. A concentrated liquid tea was prepared by concentrating the mixture to 60%.

From the foregoing description, those having ordinary skill in the art to which the present disclosure belongs will be able to understand that the present disclosure can be implemented in other specific forms without changing its technical idea or essential features. In this regard, it should be understood that the exemplary embodiments described above are only illustrative, not restrictive. The scope of the present disclosure should be interpreted as including the meaning and scope of the appended claims and all changes or modifications derived from their equivalents.

The invention claimed is:

1. A method for treating obesity by administering a composition comprising a *Gynostemma pentaphyllum* tea or a *Gynostemma pentaphyllum* tea extract, which comprises gypenoside L and gypenoside LI at a weight ratio of 100:20-80;

wherein the *Gynostemma pentaphyllum* tea or the *Gynostemma pentaphyllum* tea extract is prepared by a method comprising:

(1) a step of putting dried *Gynostemma pentaphyllum* leaf in a reaction vessel and supplying 0.1-10 parts by weight of water based on 1 part by weight of the dried *Gynostemma pentaphyllum* leaf;

(2) a step of swelling the *Gynostemma pentaphyllum* leaf while heating the reaction vessel from 100 to 150° C. at a rate of 0.2-10° C./min;

(3) a step of heating the reaction vessel at 100-150° C. for 2 minutes to 24 hours; and (4) a step of drying the swollen *Gynostemma pentaphyllum* leaf by releasing the pressure of the reaction vessel.

2. The method for treating obesity according to claim 1, wherein the *Gynostemma pentaphyllum* tea or the *Gynostemma pentaphyllum* tea extract comprises 20-140 mg/g of the gypenoside L and the gypenoside LI, comprises 10-80 mg/g of the gypenoside L and 10-60 mg/g of the gypenoside LI.

3. The method for treating obesity according to claim 1, wherein the *Gynostemma pentaphyllum* tea or the *Gynostemma pentaphyllum* tea extract comprises 0.5-14 mg/g of ginsenoside Rg3, 15-80 mg/g of gypenoside L, 10-60 mg/g of gypenoside LI, 10-20 mg/g of damulin A, 10-20 mg/g of damulin B and 10 ppb or less of benzopyrenes.

4. The method for treating obesity according to claim 1, wherein the *Gynostemma pentaphyllum* tea extract is prepared by a method further comprising a step of extracting the *Gynostemma pentaphyllum* leaf dried in the step (4) at 40-100° C. using hot water or ethanol.

5. The method of claim 1, wherein the *Gynostemma pentaphyllum* tea or the *Gynostemma pentaphyllum* tea extract further comprises 50-90 parts by weight of damulin A and damulin B based on 100 parts by weight of the gypenoside L and the gypenoside LI.

6. A method for preparing a *Gynostemma pentaphyllum* tea or a *Gynostemma pentaphyllum* tea extract for antiobesity, comprising:

(1) a step of putting dried *Gynostemma pentaphyllum* leaf in a reaction vessel and supplying 0.1-10 parts by weight of water based on 1 part by weight of the dried *Gynostemma pentaphyllum* leaf;

(2) a step of swelling the *Gynostemma pentaphyllum* leaf while heating the reaction vessel from 100 to 150° C. at a rate of 0.2-10° C./min;

(3) a step of heating the reaction vessel at 100-150° C. for 2 minutes to 24 hours; and (4) a step of drying the swollen *Gynostemma pentaphyllum* leaf by releasing the pressure of the reaction vessel, wherein the *Gynostemma pentaphyllum* tea or the *Gynostemma pentaphyllum* tea extract comprises gypenoside L and gypenoside LI at a weight ratio of 100:20-80.

7. The method of claim 6, wherein the *Gynostemma pentaphyllum* tea or the *Gynostemma pentaphyllum* tea extract further comprises 50-90 parts by weight of damulin A and damulin B based on 100 parts by weight of the gypenoside L and the gypenoside LI.

8. The method for preparing a *Gynostemma pentaphyllum* tea or a *Gynostemma pentaphyllum* tea extract for antiobesity according to claim 6, wherein the *Gynostemma pentaphyllum* tea or the *Gynostemma pentaphyllum* tea extract comprises 20-140 mg/g of the gypenoside L and the gypenoside LI, comprises 10-80 mg/g of the gypenoside L and 10-60 mg/g of the gypenoside LI.

9. The method for preparing a *Gynostemma pentaphyllum* tea or a *Gynostemma pentaphyllum* tea extract for antiobesity according to claim 8, wherein the *Gynostemma pentaphyllum* tea or the *Gynostemma pentaphyllum* tea extract comprises 0.5-14 mg/g of ginsenoside Rg3, 15-80 mg/g of gypenoside L, 10-60 mg/g of gypenoside LI, 10-20 mg/g of damulin A, 10-20 mg/g of damulin B and 10 ppb or less of benzopyrenes.

* * * * *